US011866789B2

(12) United States Patent
Byron et al.

(10) Patent No.: US 11,866,789 B2
(45) Date of Patent: *Jan. 9, 2024

(54) TARGETED THERAPIES FOR CANCER

(71) Applicants: THE TRANSLATIONAL GENOMICS RESEARCH INSTITUTE, Phoenix, AZ (US); MAYO FOUNDATION FOR MEDICAL EDUCATION AND RESEARCH, Rochester, MN (US)

(72) Inventors: Sara Byron, Phoenix, AZ (US); Jessica Aldrich, Phoenix, AZ (US); John Carpten, Phoenix, AZ (US); David Craig, Phoenix, AZ (US); Mitesh Borad, Scottsdale, AZ (US); Alan Bryce, Scottsdale, AZ (US); Michael Barrett, Scottsdale, AZ (US); George Vasmatzis, Rochester, MN (US); Keith Stewart, Scottsdale, AZ (US)

(73) Assignee: The Translational Genomics Research Institute, Phoenix, AZ (US)

( * ) Notice: Subject to any disclaimer, the term of this patent is extended or adjusted under 35 U.S.C. 154(b) by 66 days.

This patent is subject to a terminal disclaimer.

(21) Appl. No.: 17/411,447

(22) Filed: Aug. 25, 2021

(65) Prior Publication Data
US 2022/0042112 A1 Feb. 10, 2022

Related U.S. Application Data

(63) Continuation of application No. 15/735,289, filed as application No. PCT/US2016/037292 on Jun. 13, 2016, now Pat. No. 11,186,875.

(60) Provisional application No. 62/174,950, filed on Jun. 12, 2015.

(51) Int. Cl.
C12Q 1/6886 (2018.01)
G01N 33/574 (2006.01)
A61K 39/395 (2006.01)

(52) U.S. Cl.
CPC ...... C12Q 1/6886 (2013.01); A61K 39/39558 (2013.01); C12Q 2600/118 (2013.01); C12Q 2600/156 (2013.01); C12Q 2600/158 (2013.01); G01N 33/57496 (2013.01); G01N 2570/00 (2013.01); G01N 2800/52 (2013.01); G01N 2800/7028 (2013.01)

(58) Field of Classification Search
None
See application file for complete search history.

(56) References Cited

U.S. PATENT DOCUMENTS 11,186,875 B2 * 11/2021 Carpten ............... C12Q 1/6886

OTHER PUBLICATIONS

Fock et al J Cell Sci. Dec. 2015. 128(23): 4306-4316 (Year: 2015).*
Shin et al Oncotarget. Sep. 2016. 7(43): 69450-69465 (Year: 2016).*
Genecards for RBPMS, available via UR :<genecards.org/cgi-bin/carddisp.pl?gene=RBPMS>, printed on Jul. 6, 2020, 1 page.
Genecards for NRG1, available via URL: <genecards.org/cgi-bin/carddisp.pl?gene=NRG1>, printed on Jul. 6, 2020, 1 page.
Bernsten et al., "Ewing's Sarcoma Family of Tumors: Current Management," The Oncologist, 2006, pp. 506-519.
Jacobs et al., Molecular Imaging of Gliomas, Moleclar Imaging, vol. 1, No. 4, Oct. 2002, pp. 309-335.
Shin, et al. (1996) Hepatitis B and C virus, Clonorchis sinensis for the risk of liver cancer: a case-control study in Pusan, Korea. International Journal of Epidemiology 25: 933-940.
Watanapa P. (1996) Cholangiocarcinoma in patients with opisthorchiasis. The British journal of surgery 83: 1062-1064.
Watanapa, et al. (2002) Liver fluke-associated cholangiocarcinoma. The British journal of surgery 89: 962-970.
Bergquist, et al. (2002) Hepatic and extrahepatic malignancies in primary sclerosing cholangitis. Journal of hepatology 36: 321-327.
Bergquist A, et al. (1998) Risk factors and clinical presentation of hepatobiliary carcinoma in patients with primary sclerosing cholangitis: a case-control study. Hepatology 27: 311-316.
Burak, et al. (2004) Incidence and risk factors for cholangiocarcinoma in primary sclerosing cholangitis. The American Journal of Gastroenterology 99: 523-526.
Claessen, et al. (2009) High lifetime risk of cancer in primary sclerosing cholangitis. Journal of Hepatology 50: 158-164.
Visser, et al. (2004) Congenital choledochal cysts in adults. Archives of Surgery 139: 855-862.
Hsing, et al. (2008) Hepatitis B and C virus infection and the risk of biliary tract cancer: a population-based study in China. International journal of cancer Journal international du cancer 122: 1849-1853.
Kobayashi, et al., (2000) Incidence of primary cholangiocellular carcinoma of the liver in japanese patients with hepatitis C virus-related cirrhosis. Cancer 88: 2471-2477.
Liu, et al. (2003) Pathogenesis of cholangiocarcinoma in the porta hepatis and infection of hepatitis virus. Hepatobiliary & Pancreatic Diseases International : HBPD INT 2: 285-289.
Shaib, et al. (2005) Risk factors of intrahepatic cholangiocarcinoma in the United States: a case-control study. Gastroenterology 128: 620-626.
Wetzel, et al. (2007) Risk factors for intrahepatic and extrahepatic cholangiocarcinoma in the United States: a population-based case-control study. Clinical Gastroenterology and Hepatology 5: 1221-1228.

(Continued)

Primary Examiner — Carla J Myers
(74) Attorney, Agent, or Firm — Noblitt & Newson, PLLC

(57) ABSTRACT

Various embodiments provide compositions and methods for detecting cancers containing an NRG1 fusion event and treating a patient with a therapeutic agent that is targeted to the NRG1 fusion. Exemplary compositions for treating cancers containing the NRG1 fusion may comprise therapeutic agents inhibiting Epidermal Growth Factor Receptor and/or ERBB2 such as cetuximab, panitumumab, Sym004, MM-151, mAb 806, mAb 528, MEHD794A, gefitinib, erlotinib, lapatinib, afatinib, PD153035, AG1478, trastuzumab, and pertuzumab. In some embodiments, the therapeutic agent may be a combination of trastuzumab, and pertuzumab.

26 Claims, 15 Drawing Sheets

(56) References Cited

OTHER PUBLICATIONS

Yamamoto, et al. (2004) Hepatitis C virus infection as a likely etiology of intrahepatic cholangiocarcinoma. Cancer Science 95: 592-595.

Donato, et al. (2001) Intrahepatic cholangiocarcinoma and hepatitis C and B virus infection, alcohol intake, and hepatolithiasis: a case-control study in Italy. Cancer Causes & Control : CCC 12: 959-964.

Lee, et al. (2002) What is the impact of coexistence of hepatolithiasis on cholangiocarcinoma? Journal of Gastroenterology and Hepatology 17: 1015-1020.

Becker, et al. (2008) Mortality among Thorotrast-exposed patients and an unexposed comparison group in the German Thorotrast study. European Journal of Cancer 44: 1259-1268.

Travis, et al. (2003) Site-specific cancer incidence and mortality after cerebral angiography with radioactive thorotrast. Radiation Research 160: 691-706.

Khan, et al. (2005) Cholangiocarcinoma. Lancet 366: 1303-1314.

Valle, et al. (2010) Cisplatin plus gemcitabine versus gemcitabine for biliary tract cancer. The New England Journal of Medicine 362: 1273-1281.

Craig, et al. (2013) Genome and transcriptome sequencing in prospective metastatic triple-negative breast cancer uncovers therapeutic vulnerabilities. Mol Cancer Ther 12: 104-116.

Christoforides, et al. (2013) Identification of somatic mutations in cancer through Bayesian-based analysis of sequenced genome pairs. BMC Genomics 14: 302.

Kim, et al. (2011) TopHat-Fusion: an algorithm for discovery of novel fusion transcripts. Genome Biology 12: R72.

Iyer, et al. (2011) ChimeraScan: a tool for identifying chimeric transcription in sequencing data. Bioinformatics 27: 2903-2904.

McPherson, et al. (2011) deFuse: an algorithm for gene fusion discovery in tumor RNA-Seq data. PLoS Computational Biology 7: e1001138.

Asmann, et al. (2011) A novel bioinformatics pipeline for identification and characterization of fusion transcripts in breast cancer and normal cell lines. Nucleic Acids Research 39: e100.

Diep, et al. (2012) Down-regulation of Yes Associated Protein 1 expression reduces cell proliferation and clonogenicity of pancreatic cancer cells. PLoS One 7: e32783.

Fernandez-Cuesta, et al. (2014) CD74-NRG1 Fusions in Lung Adenocarcinoma. Cancer Discovery 4(4): 415-422.

Nakaoku, et al. (2014) Druggable Oncogene Fusions In Invasive Mucinous Lung Adenocarcinoma. Clinical Cancer Research 12: 3087-93.

Dhanasekaran, et al. (2014) Transcriptome meta-analysis of lung cancer reveals recurrent aberrations in NRG1 and Hippo pathway genes. Nature Communications 5: 5893.

Fernandez-Cuesta, et al. (2015) Molecular Pathways: Targeting NRG1 Fusions in Lung Cancer. Clinical Cancer Research 21(9): 1989-94.

Balbin, OA, "Identifying Novel Targetable Genes and Pathways in Cancer by Integrating Diverse Omics Data," Dissertation at the University of Michigan, 2014, p. 94.

Scheuer et al., "Strongly Enhanced Antitumor Activity of Trastuzumab and Pertuzumab Combination Treatment on HER2-Positive Human Xenograft Tumor Models," Cancer Res 2009; 69: (24). Dec. 15, 2009.

Javle et al., HER2/neu-directed therapy for biliary tract cancer, Journal of Hematology & Oncology (2015) 8:58.

\* cited by examiner

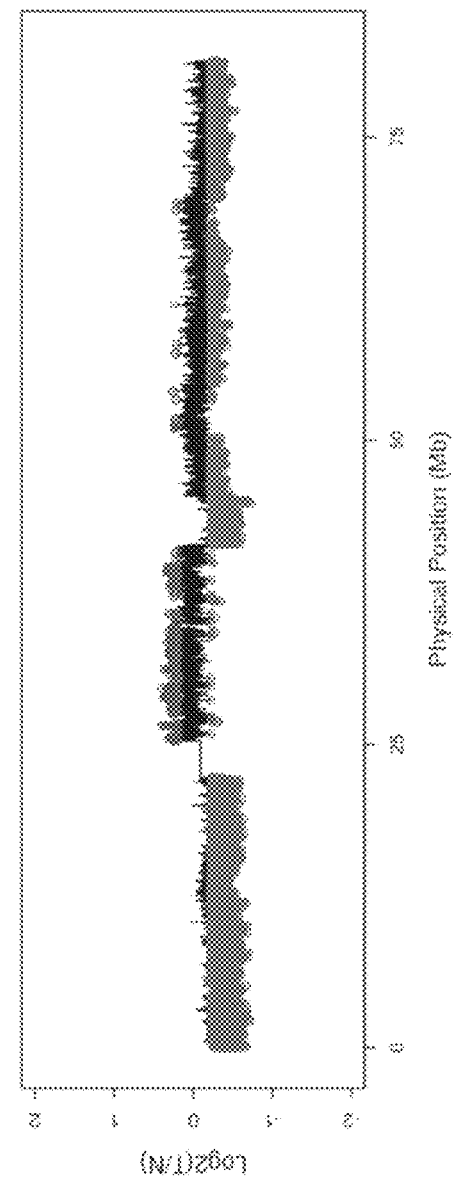
Figure 1Q
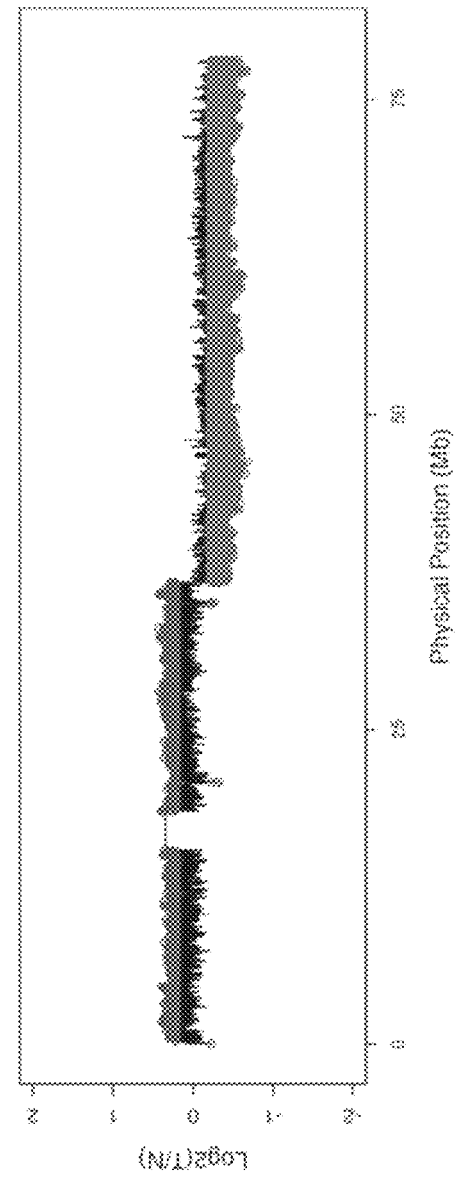
Figure 1R
Figure 1 continued

Figure 1 continued
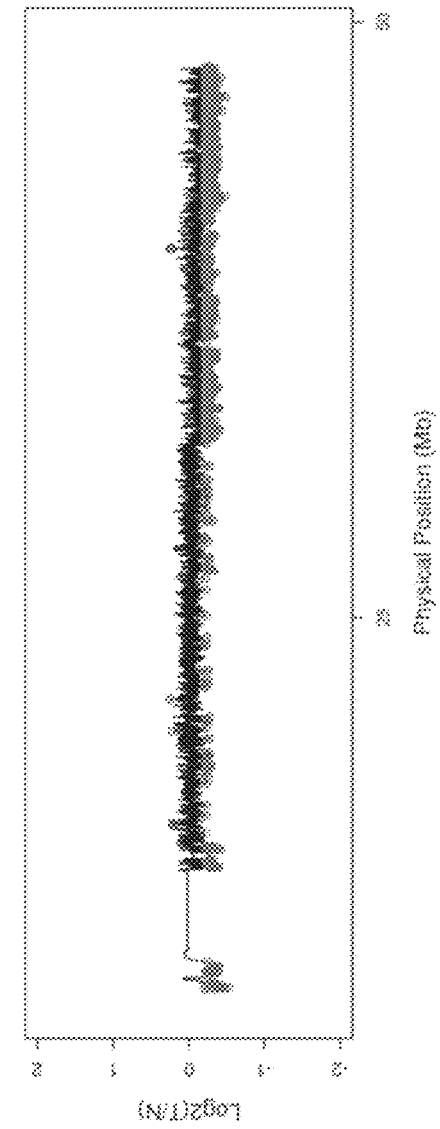
Figure 1U
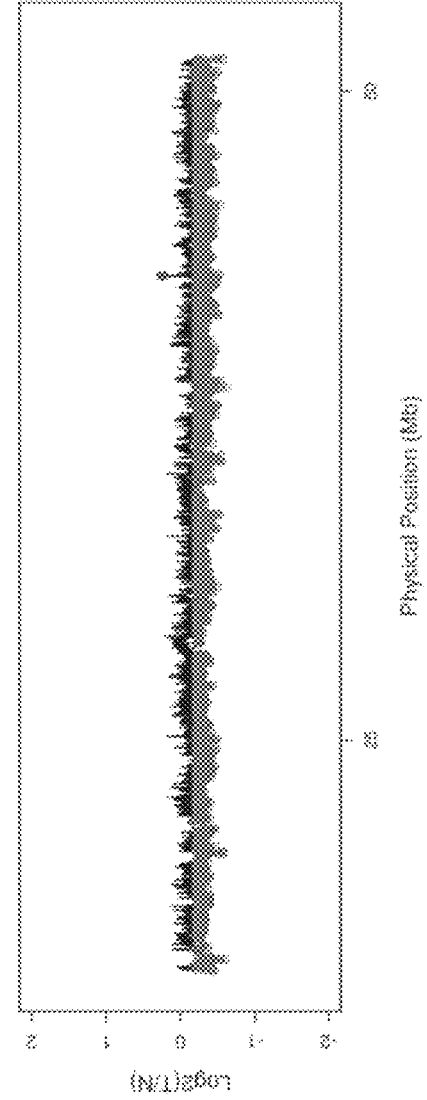
Figure 1V

After 8 Weeks of Treatment

Baseline

After 8 Weeks of Treatment

Baseline

TARGETED THERAPIES FOR CANCER

CROSS-REFERENCE TO RELATED APPLICATIONS

This application is a continuation application of U.S. patent application Ser. No. 15/735,289, filed Dec. 11, 2017, entitled "Targeted Therapies for Cancer", which is a U.S. National Stage filing of PCT/US16/37292, filed Jun. 13, 2016, entitled "Targeted Therapies for Cancer", which claims the benefit of and priority to U.S. Provisional Patent Application No. 62/174,950, filed Jun. 12, 2015, all of which are incorporated by reference.

BACKGROUND

Biliary tract cancers (BTC) comprise malignant tumors of the intrahepatic and extrahepatic bile ducts. Known risk factors for BTC are the liver flukes *O. viverrini* and *C. sinensis* in high prevalence endemic regions in southeast Asia (See References 1-3), as well as primary sclerosing cholangitis (See References 4-7), Caroli's disease (See Reference 8), hepatitis B and hepatitis C (See References 9-14), obesity (See Reference 13), hepatolithiasis (See References 15 and 16), and thorotrast contrast exposure (See References 17 and 18). Surgical approaches such as resection and liver transplantation represent the only curative treatment approaches for BTC (See Reference 19).

Unfortunately, the majority of BTC are diagnosed at advanced stages of the disease when symptoms arise and the tumor is surgically unresectable and/or metastatic disease has already occurred. Systemic therapy with gemcitabine and cisplatin has been established as the standard of care for patients with advanced disease, but is only palliative (See Reference 20), emphasizing the imminent need for novel therapies.

SUMMARY

Various embodiments provide compositions and methods for detecting cancers containing an NRG1 somatic gene fusion event and treating a patient with a therapeutic agent that is targeted to the NRG1 fusion. Exemplary compositions for treating cancers containing the NRG1 fusion may comprise therapeutic agents inhibiting Epidermal Growth Factor Receptor and/or ERBB2 such as cetuximab, panitumumab, Sym004, MM-151, mAb 806, mAb 528, MEHD794A, gefitinib, erlotinib, lapatinib, afatinib, PD153035, AG1478, trastuzumab, and pertuzumab. In some embodiments, the therapeutic agent may be a combination of trastuzumab, and pertuzumab.

BRIEF DESCRIPTION OF THE DRAWINGS

A more complete understanding of the present technology may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. For example, steps that may be performed concurrently or in different order are illustrated in the figures to help to improve understanding of embodiments of the present technology.

Figure 1A:
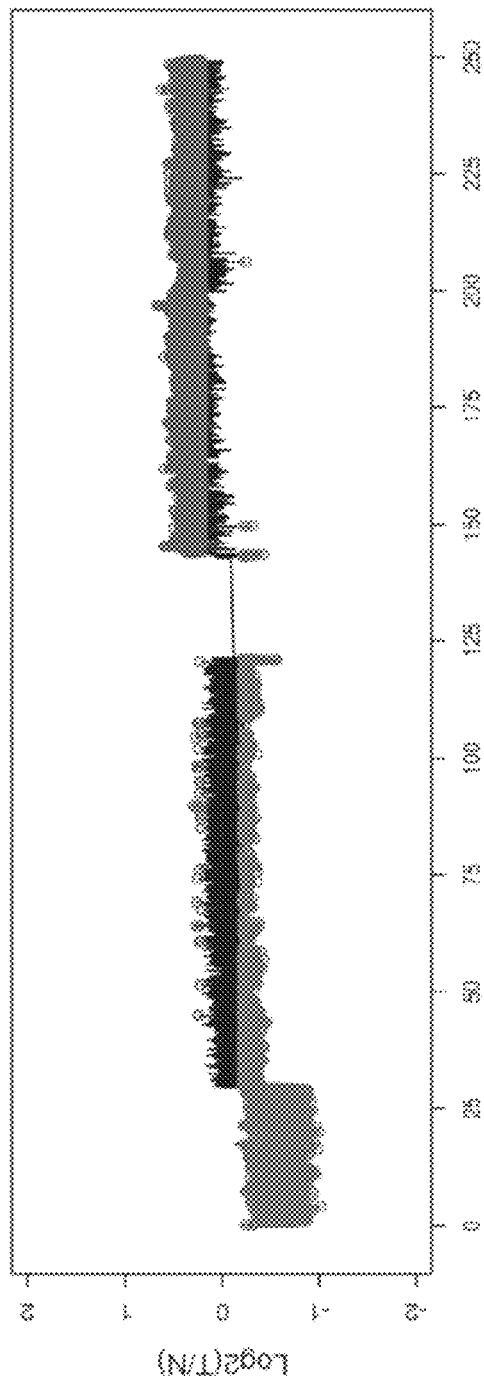
Figure 1B:
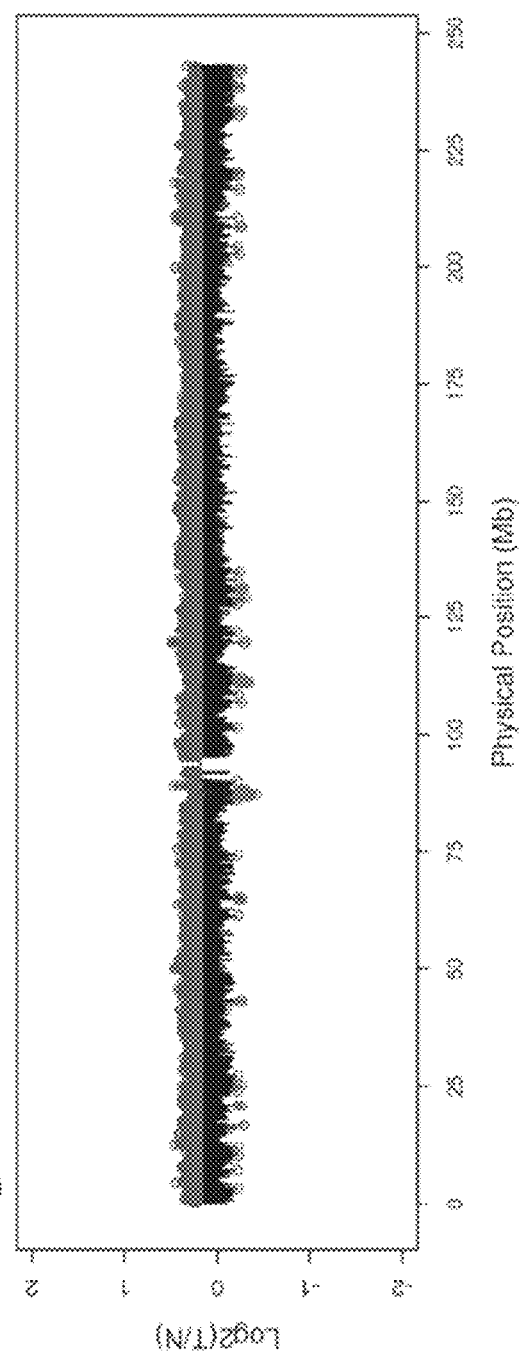
Figure 1C:
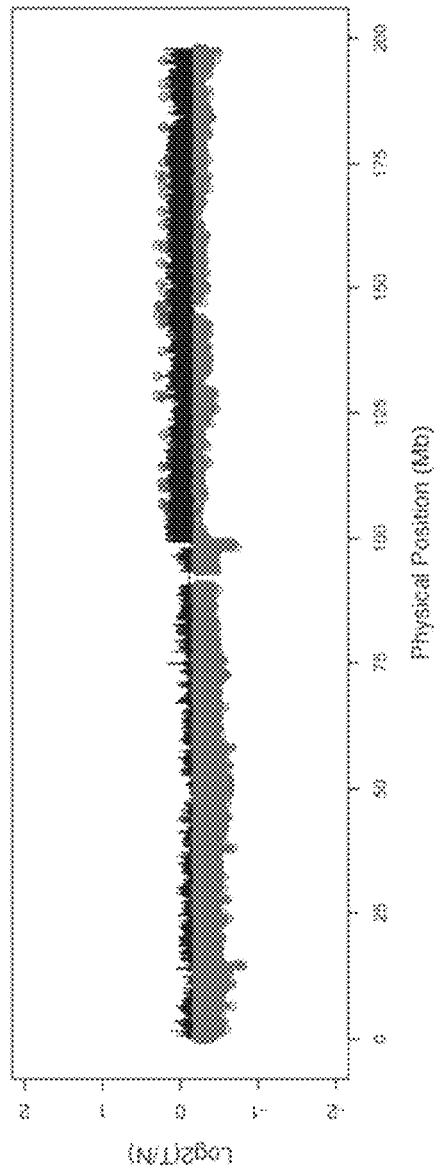
Figure 1D:
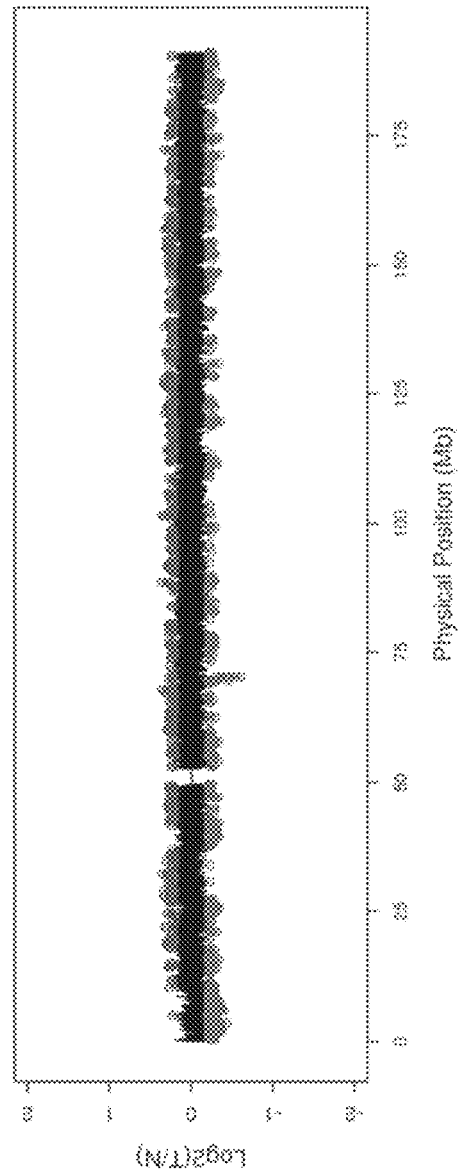
Figure 1E:
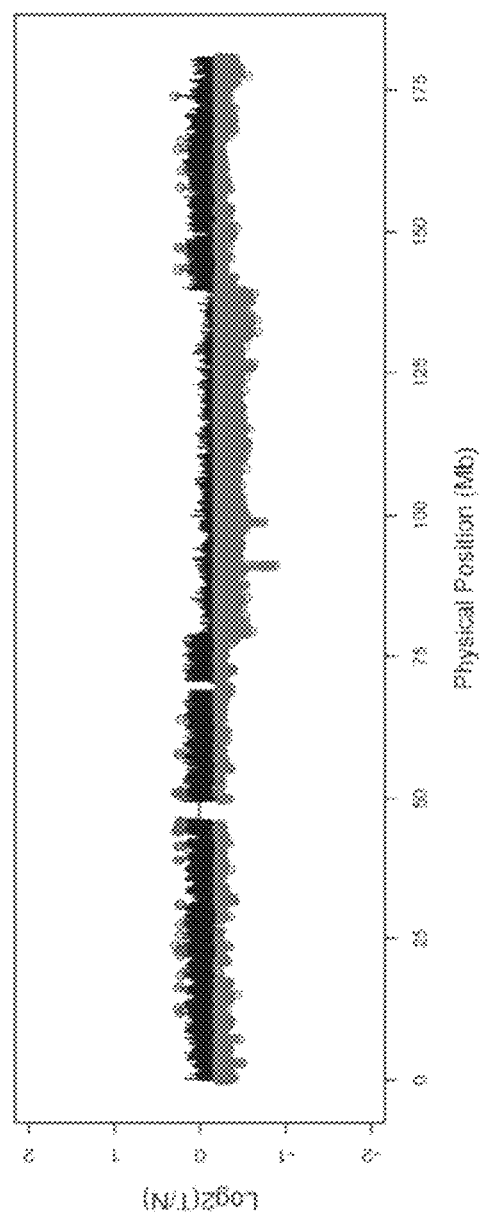
Figure 1F:
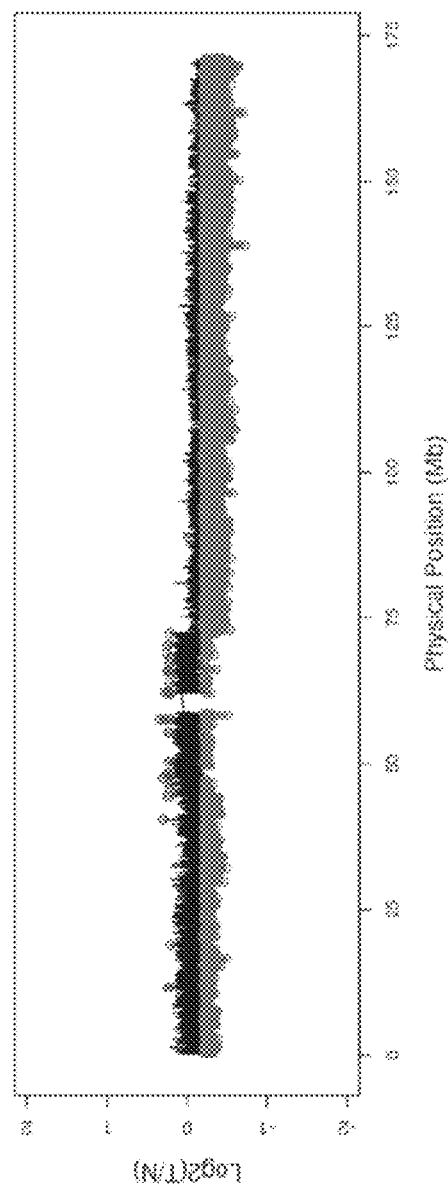
Figure 1G:
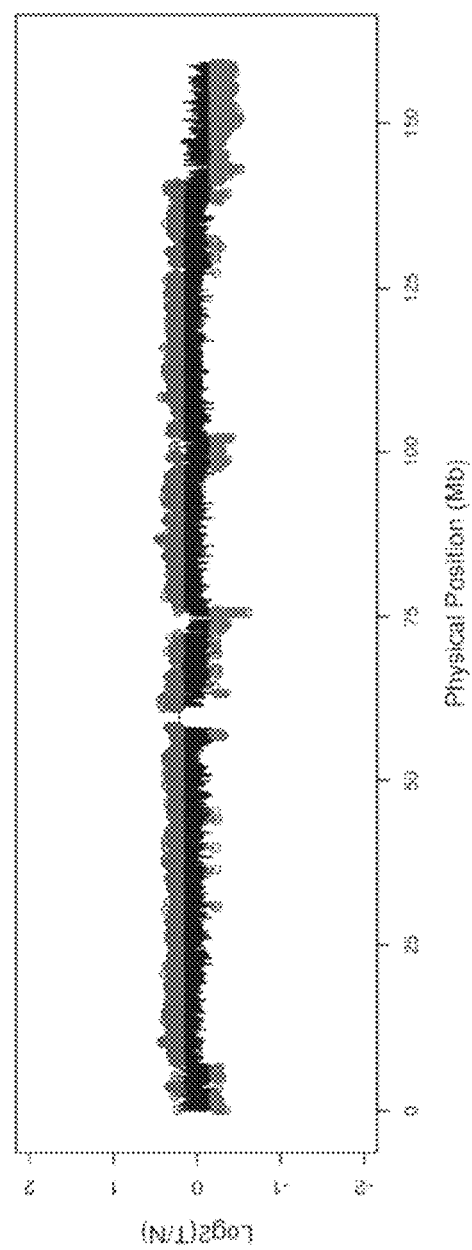
Figure 1H:
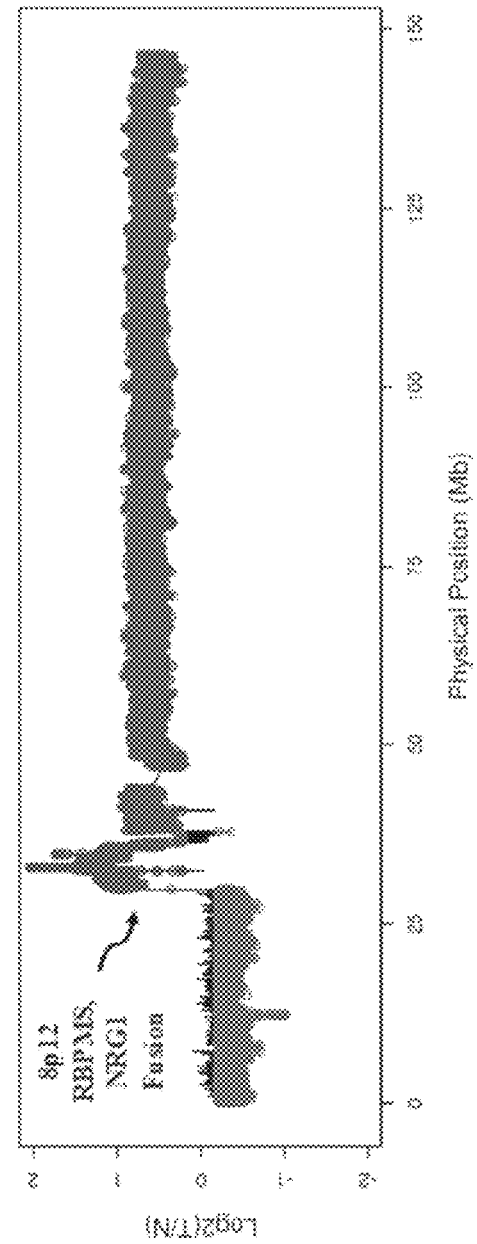
Figure 1I:
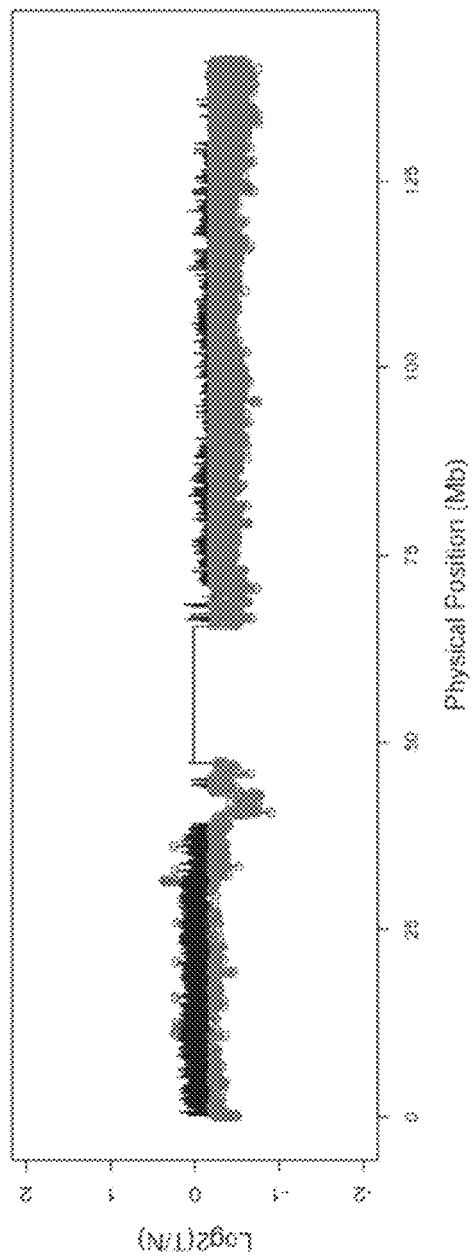
Figure 1J:
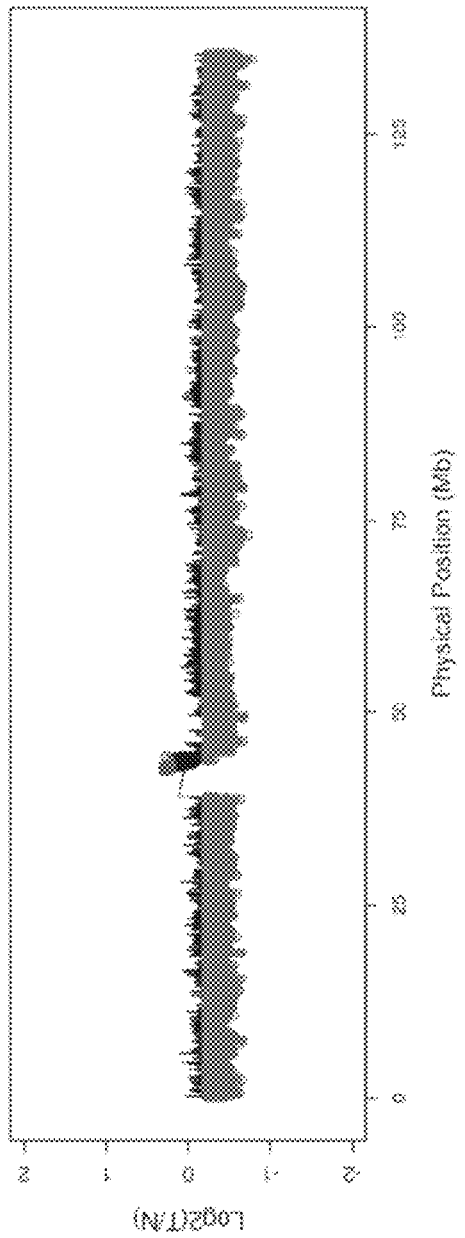
Figure 1K:
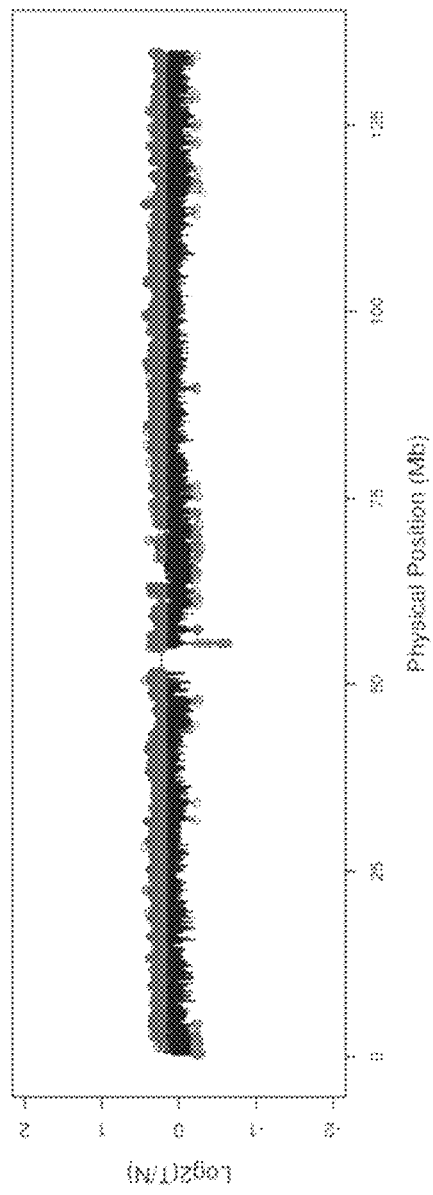
Figure 1L:
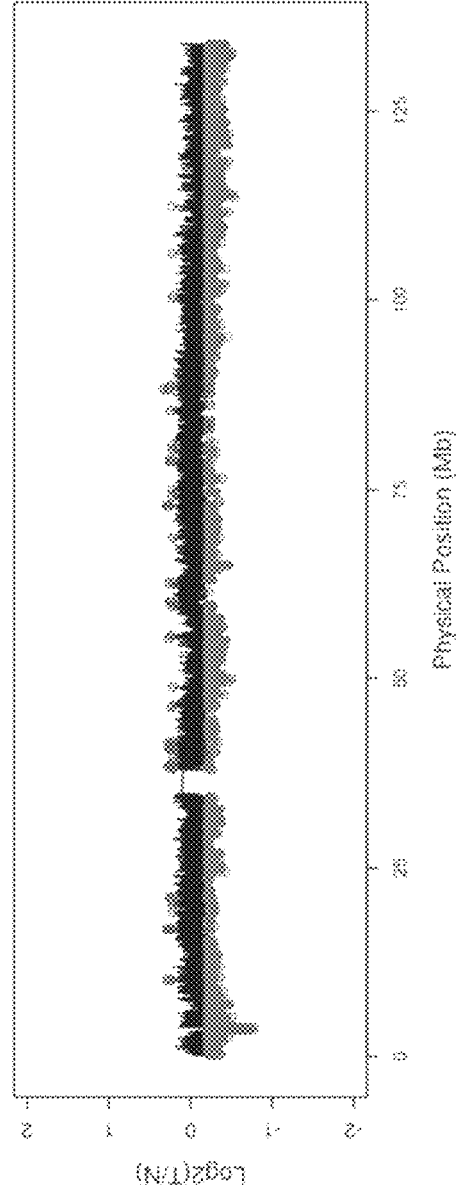
Figure 1M:
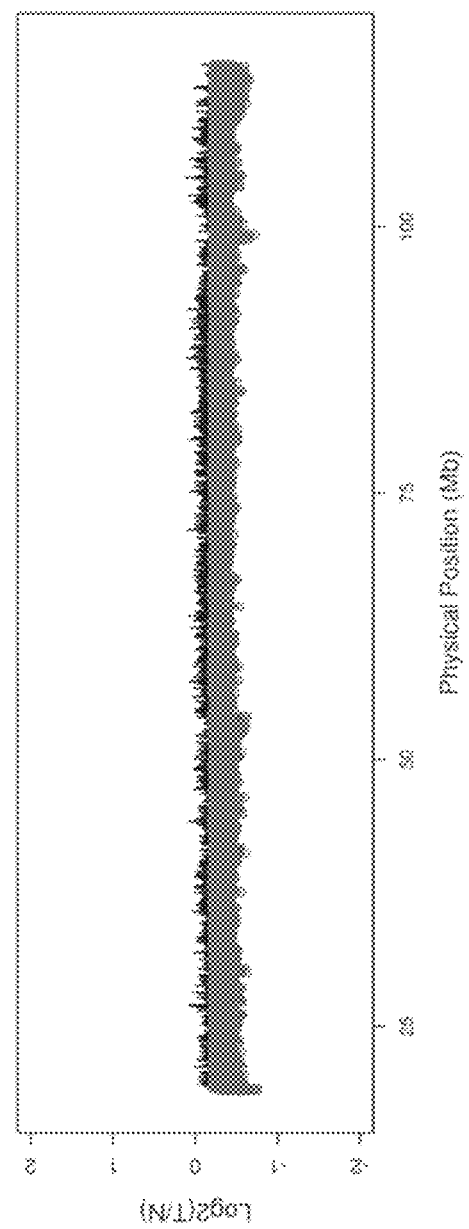
Figure 1N:
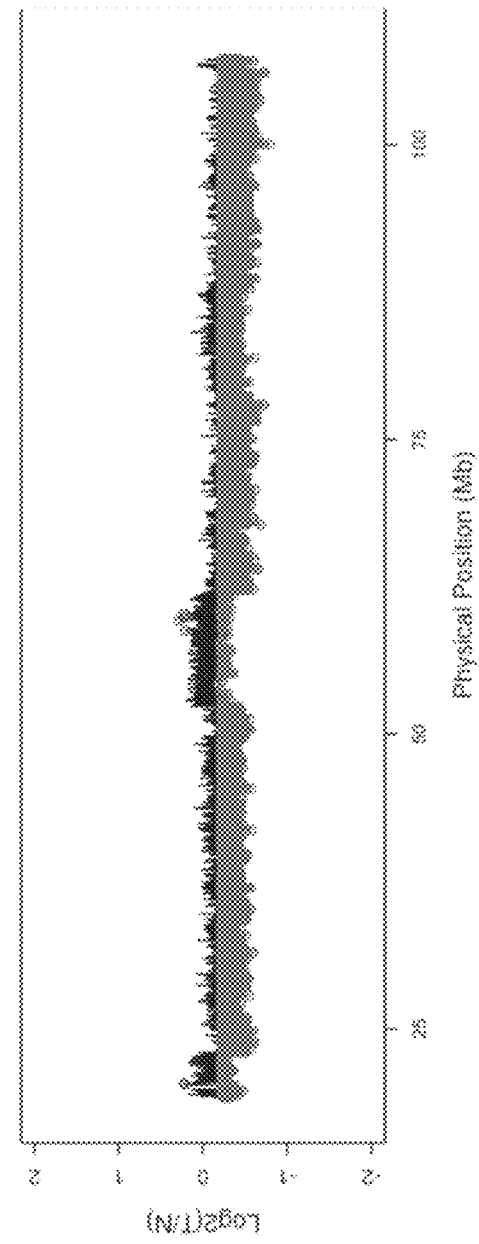
Figure 1O:
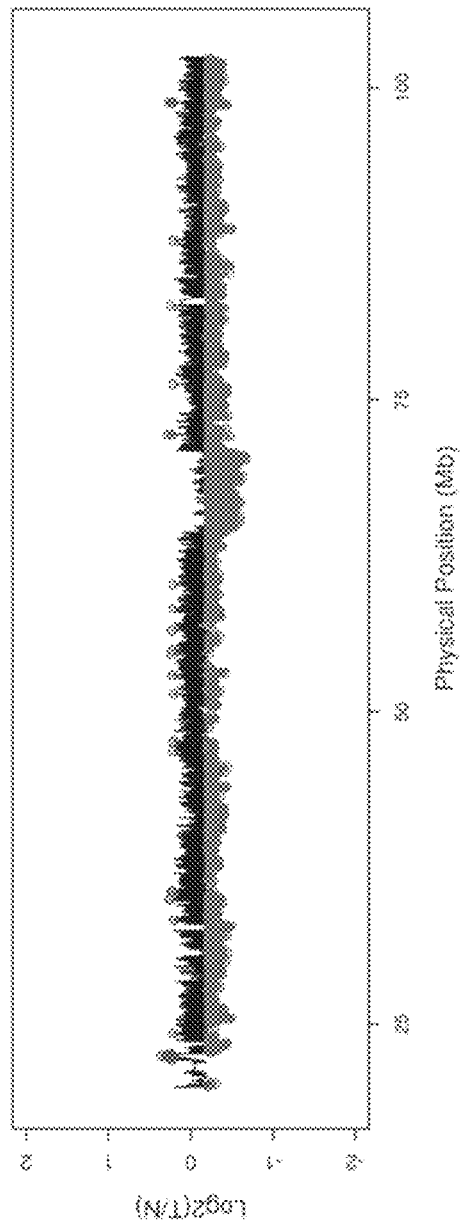
Figure 1P:
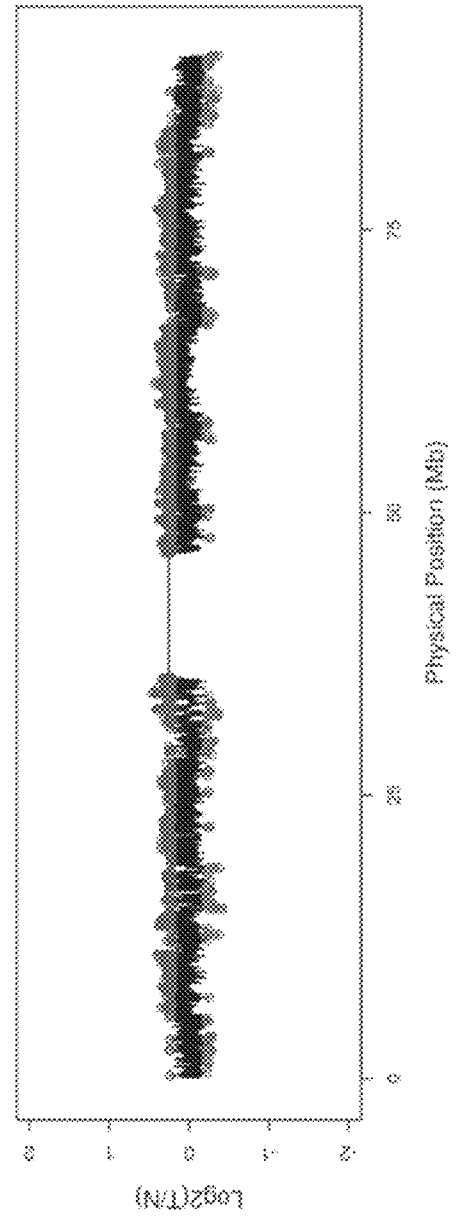
Figure 1:
Figure 1:
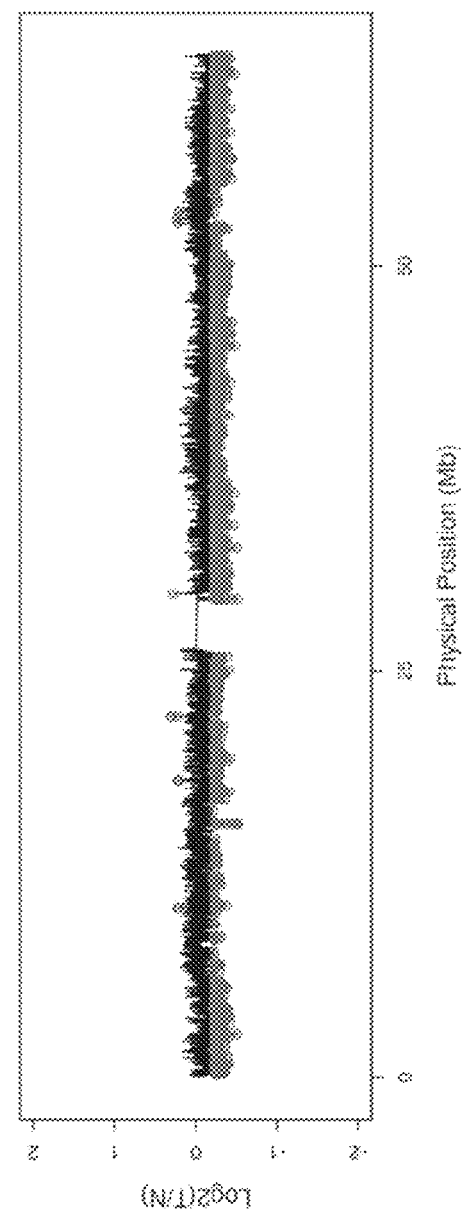
Figure 1:
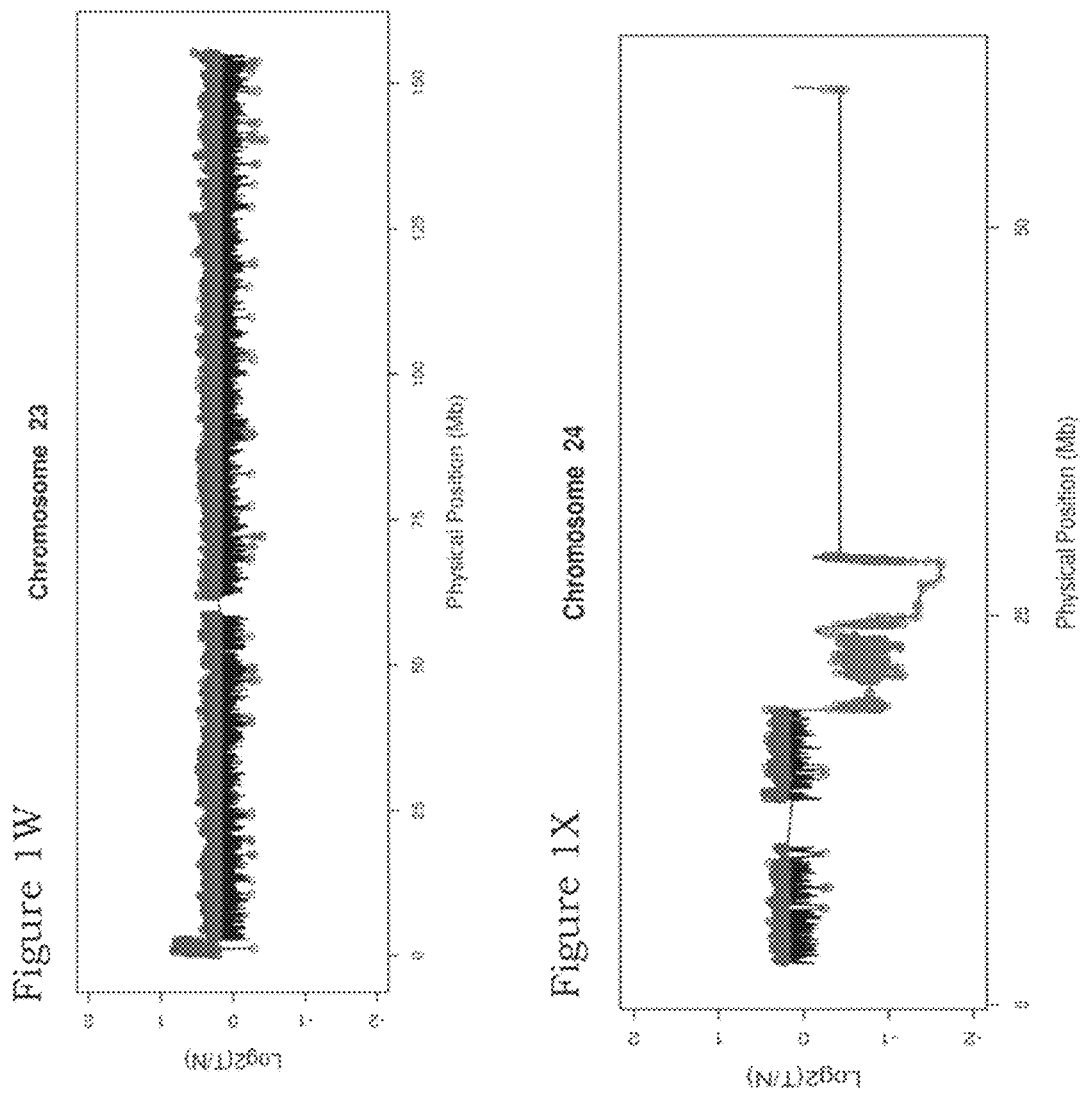
Figure 2:
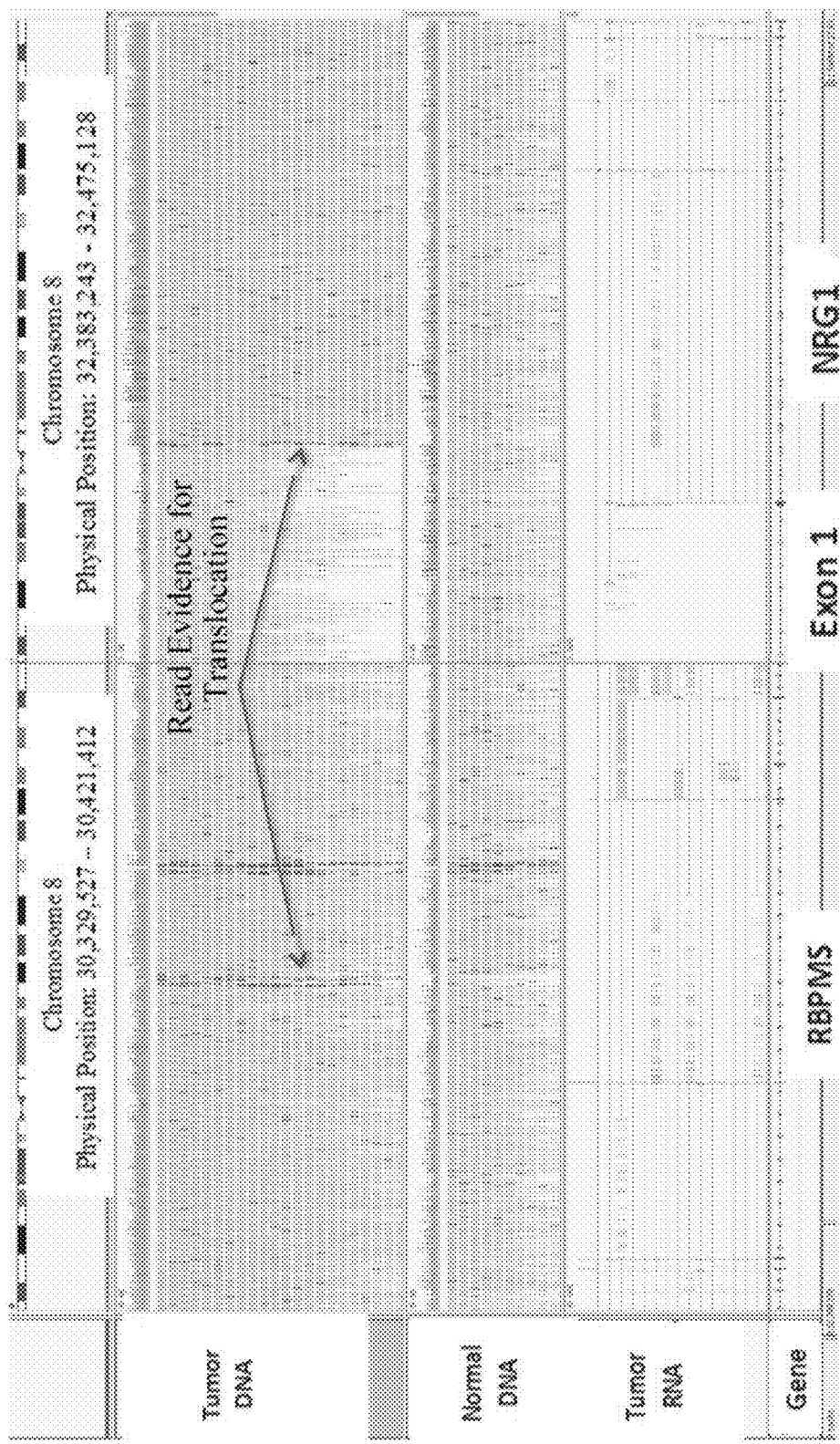
Figure 3:
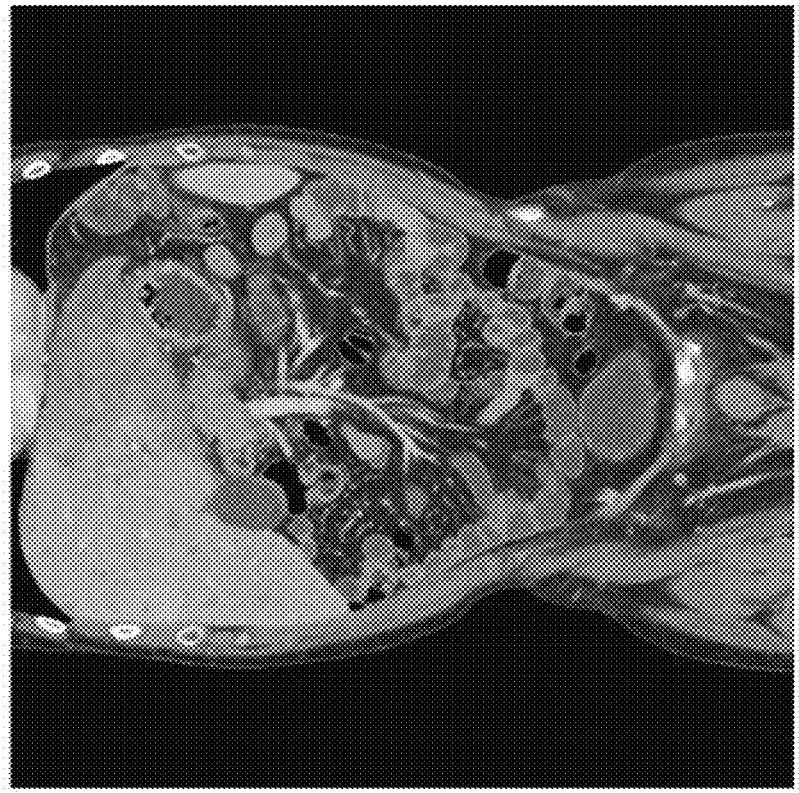
Figure 3:
Figure 4:
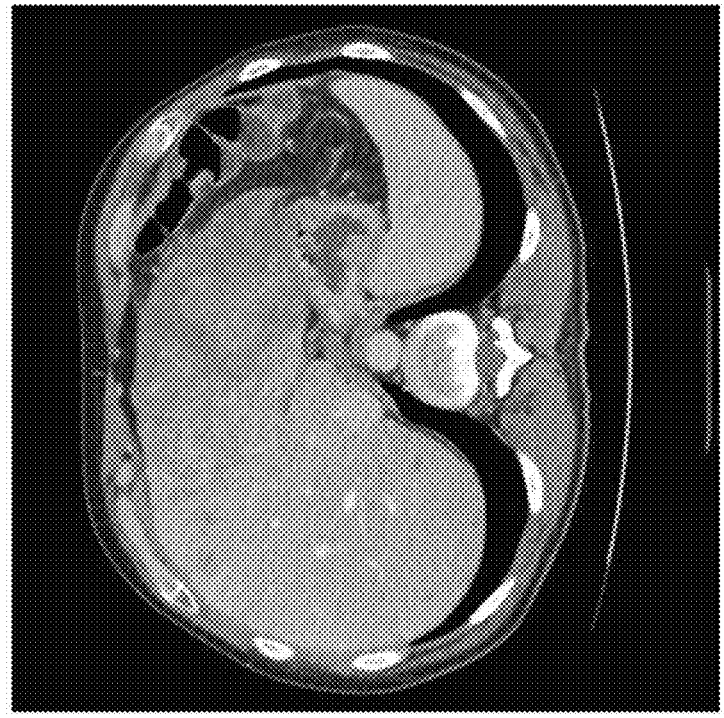
Figure 4:
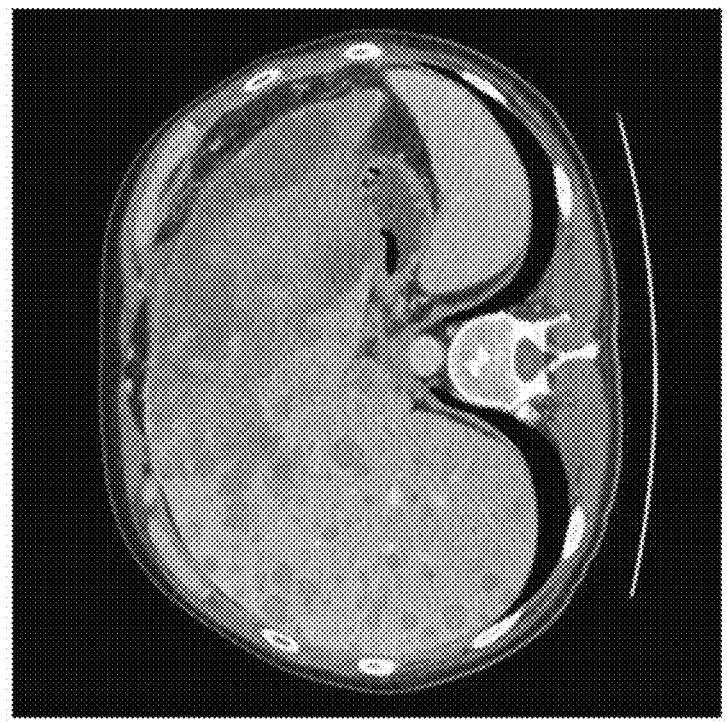

The figures described are for illustration purposes only and are not intended to limit the scope of the present disclosure in any way. Various aspects of the present technology may be more fully understood from the detailed description and the accompanying drawing figures, wherein:

FIG. 1A-1X representatively illustrates a schematic of DNA copy number within each chromosome of a cholangiocarcinoma tumor in relation to a normal reference genome, wherein, FIG. 1A illustrates the schematic of DNA copy number for chromosome 1; FIG. 1B illustrates the schematic of DNA copy number for chromosome 2; FIG. 1C illustrates the schematic of DNA copy number for chromosome 3; FIG. 1D illustrates the schematic of DNA copy number for chromosome 4; FIG. 1E illustrates the schematic of DNA copy number for chromosome 5; FIG. 1F illustrates the schematic of DNA copy number for chromosome 6; FIG. 1G illustrates the schematic of DNA copy number for chromosome 7; FIG. 1H illustrates the schematic of DNA copy number for chromosome 8; FIG. 1I illustrates the schematic of DNA copy number for chromosome 9; FIG. 1J illustrates the schematic of DNA copy number for chromosome 10; FIG. 1K illustrates the schematic of DNA copy number for chromosome 11; FIG. 1L illustrates the schematic of DNA copy number for chromosome 12; FIG. 1M illustrates the schematic of DNA copy number for chromosome 13; FIG. 1N illustrates the schematic of DNA copy number for chromosome 14; FIG. 1O illustrates the schematic of DNA copy number for chromosome 15; FIG. 1P illustrates the schematic of DNA copy number for chromosome 16; FIG. 1Q illustrates the schematic of DNA copy number for chromosome 17; FIG. 1R illustrates the schematic of DNA copy number for chromosome 18; FIG. 1S illustrates the schematic of DNA copy number for chromosome 19; FIG. 1T illustrates the schematic of DNA copy number for chromosome 20; FIG. 1U illustrates the schematic of DNA copy number for chromosome 21; FIG. 1V illustrates the schematic of DNA copy number for chromosome 22; FIG. 1W illustrates the schematic of DNA copy number for chromosome 23; and FIG. 1X illustrates the schematic of DNA copy number for chromosome 24;

FIG. 2 representatively illustrates a schematic of DNA copy number showing DNA translocation in chromosome 8 of the cholangiocarcinoma tumor;

FIG. 3 is a PET scan image of a front view of a patient showing shrinkage of a cholangiocarcinoma tumor containing a NGR1 gene fusion in response to treatment with pertuzumab and trastuzumab; and FIG. 4 is a PET scan image of a cross-sectional view of a patient showing shrinkage of a cholangiocarcinoma tumor containing a NGR1 gene fusion in response to treatment with pertuzumab and trastuzumab.

DETAILED DESCRIPTION OF EXEMPLARY EMBODIMENTS

The present technology may be described in terms of functional block components and various processing steps. Such functional blocks may be realized by any number of components configured to perform the specified functions and achieve the various results. For example, methods and systems according to various aspects of the present technology may be practiced in conjunction with any number of systems and methods for diagnosing and/or treating cancer in humans and animals and the systems described are merely some exemplary applications for the technology.

The particular implementations shown and described are illustrative of the technology and its best mode and are not intended to otherwise limit the scope of the present technology in any way. For the sake of brevity, conventional manufacturing, processing, preparation, sterilization, and other functional aspects of the system may not be described in detail. Various aspects of the technology provide methods for using pharmaceutical compositions for treating cancers containing NRG1 somatic gene fusion events (hereinafter "NRG1 fusion.") A detailed description of various embodiments is provided as a specific enabling disclosure that may be generalized to any application of the disclosed systems and methods in accordance with the various described embodiments.

Various embodiments of the present technology provide methodologies for the treatment of cancer. In some aspects, the methodologies may include a method of treating a patient with cancer, which may include analyzing a sample from the patient with cancer to detect the presence or absence of an NRG1 fusion. Thereafter, the methodology may include treating the patient with a therapeutic agent that is targeted to the NRG1 fusion.

In various embodiments, the cancer may be any cancer or any other disease for which a phenotype brought about by an NRG1 fusion may be a therapeutic target. For example, cancers containing the NRG1 fusion may include a biliary tract cancer (BTC), hepatocellular cancer, colon cancer, breast cancer, pancreatic cancer, lung cancer, and ovarian cancer. In some cases, a BTC containing a NRG1 fusion may be characterized as cholangiocarcinoma.

Moreover, in some aspects, the methodologies for detection of the NRG1 fusion may comprise analyzing a patient sample, such as a tumor biopsy, by at least one of the following: whole genome sequencing, whole exome sequencing, whole transcriptome sequencing, or any another related methodologies, including other sequencing methodologies. Further, the methodologies may also comprise assessing the effects of treatment with the therapeutic agent on the cancer through diagnostic imagery of the patient, such as ultrasound and/or tomography, following a course of treatment with the therapeutic agent.

In various embodiments of the present technology, NRG1 fusions may be found in cholangiocarcinoma tumors. Cholangiocarcinoma is a cancer that affects the bile ducts. This cancer may form in the small tubes of the bile ducts within the liver that carry bile to the gallbladder (intrahepatic bile ducts) or the cancer may develop in bile ducts outside of the liver (extrahepatic bile ducts). Due to the delay in the onset of symptoms such as pain from bile duct obstruction, many patients diagnosed with cholangiocarcinoma have advanced disease that cannot be treated with surgery because the cancer has spread to other parts of the body, thus severely limiting treatment options.

In various embodiments of the present technology, methods disclosed herein enable treatment of NRG1 fusion containing cancers with therapeutic agents that provide "targeted therapy" that exploits an error in the normal functioning of these tumor cells, compared to other cells in the body, thus allowing primarily tumor cells to be killed by the drug. During the course of a clinical trial with patients diagnosed with advanced cholangiocarcinoma, integrated genome-wide, exome, and whole transcriptome/RNA sequencing sequence analyses were performed on patient tumors to identify potential therapeutically actionable genetic abnormalities. Among the somatic events captured in the analysis of patient tumors, therapeutically relevant genomic changes were identified that, when treated with the therapeutic agent, exhibited evidence of anti-tumor activity.

As such, the present application provides methods of identifying patient populations within a pool of cancer patients that respond to a targeted therapy. For example, in some embodiments, the methods may comprise identifying a genomic aberration in a patient with cancer (e.g., cholangiocarcinoma) and administering a targeted therapy to the patient. In some aspects, the genomic aberration may be a deletion, amplification, fusion, or any other form of genetic alteration. By way of example only, in some aspects, the genomic aberration may be a fusion of two or more genes. In some embodiments, at least one of the fused genes may be NRG1 and the second of the fused genes may be any other gene that is known or unknown to induce oncogenic changes in a patient. For example, the fusion may be an NRG1-RBPMS fusion.

The RNA binding protein with multiple splicing, encoded by the RBPMS gene, encodes a member of the RRM family of RNA-binding proteins. RBPMS contains an RNA recognition motif (RRM) for binding RNA. The RRM domain is between 80-100 amino acids in length and family, members can contain one to four copies of the domain. The RRM domain consists of two short stretches of conserved sequence called RNP1 and RNP2, as well as a few highly conserved hydrophobic residues. The protein encoded by this gene has a single, putative RRM domain in its N-terminus. Alternative splicing results in multiple variants encoding different isoforms.

Neuregulin 1, or NRG1, is a 44 kD glycoprotein that is a ligand to ERBB2 and ERBB4 family members of the HER/ERBB protein family. NRG1 interacts with the NEU/ERBB2 receptor tyrosine kinase to increase its phosphorylation of tyrosine residues. Binding of NRG1 to ERBB3 and ERBB4 induces heterodimerization of these proteins with ERBB1 (i.e., Epidermal growth factor receptor or EGFR) and ERBB2. These heterodimers are thereby phosphorylated and propagate a signaling cascade leading to cellular proliferation, migration, and invasion which are all hallmarks of oncogenesis. Moreover, this signaling cascade mediates cell-cell interactions and plays crucial roles in the growth and development of multiple organ systems.

The RBPMS-RGI fusion contains NRG1 as the 3-primer partner and retains its EGF-like domain that is essential for receptor interactions. Though not yet demonstrated for the RBPMS-NRG1 fusion, other NRG1 fusions that retain the EGF-like domain of NRG1 have been shown to activate HER2:HER3 signaling (See Reference 29), and, in lung tumors, presence of the CD74-NRG1 fusion was strongly associated with increased phospho-ERBB3 by immunohistochemistry (See Reference 28). Cell line models expressing NRG1 fusions show increased sensitivity to ERBB2 kinase inhibitors, including Afatinib and Lapatinib (See Reference 29). Due to potential reactivation of ERBB3 as a mechanism of resistance to exclusive targeting of ERBB2, blocking ERBB2-ERBB3 heterodimerization with Pertuzumab has also been proposed as a strategy for targeting NRG1 fusions (See Reference 31). Clinical efficacy of these approaches in the context of NRG1 fusions remains to be demonstrated. Lapatinib was previously tested in a phase 2 trial in patients with advanced biliary tract cancer or hepatobiliary cancer, and there was no objective response in the 17 patients evaluated.

Some embodiments of the technology may also provide a method of inhibiting cancer cell growth, which may include contacting a cancer cell containing an NRG1 fusion with at least one therapeutic agent selected from the following groups: an Epidermal Growth Factor Receptor (EGFR) inhibitor and an inhibitor of ERBB2. For example, the EGFR inhibitor may be selected from the group consisting of: cetuximab, panitumumab, erlotinib, gefitinib, lapatinib, and afatinib and the ERBB2 inhibitor can be selected from the group consisting of: lapatinib, afatinib, trastuzumab, and pertuzumab. In some aspects, the inhibitor may be a combination of trastuzumab and pertuzumab.

Some embodiments of the technology may comprise treating a patient with a cancer using one or more therapeutics that may be targeted to one or more genomic aberrations within the patient. For example, in some aspects, the genomic aberration may comprise an NRG1 fusion such that one or more therapeutics targeted to NRG1, one or more binding partners of NRG1, and/or one or more upstream or downstream members of the NRG1-related signaling cascade. In some aspects, the targeted therapeutics may comprise one or more active agents (e.g., small molecule drugs, antibodies, biologics, etc.) that target EGFR/ERBB1, such as one or more of cetuximab, panitumumab, Sym004, MM-151, mAb 806, mAb 528, MEHD794A, gefitinib, erlotinib, lapatinib, afatinib, PD153035, AG1478, or any other agents that target EGFR. In additional aspects, the target therapeutics may comprise one or more active agents that target ERBB2, such as trastuzumab, pertuzumab, lapatinib, and afatinib. In other embodiments, the targeted therapeutics may comprise one or more of the active agents listed above in any combination and/or may further comprise other active agents that can potentially treat the cancer.

Various methods of detecting the NGR1 gene fusion in a patient sample containing cancer and selecting a chemotherapy regimen for treatment of cancer containing the NGR1 gene fusion are disclosed. The methods of detection and treatment may comprise any number of conventional techniques for the collection and processing of biological samples from patients in preparation for genetic analysis. An exemplary embodiment of detecting the NGR1 fusion in a patient with cholangiocarcinoma and selecting a chemotherapy regimen for treatment of the cholangiocarcinoma may comprise the steps of: (i) collecting a patient genetic sample from a cholangiocarcinoma tumor; (ii) analyzing the genetic sample for a NRG1 fusion; and (iii) selecting a therapeutic agent comprising an inhibitor of ERBB2 and/or EGFR if the NRG1 fusion is present. For example, the EGFR inhibitor may be selected from the group consisting of cetuximab, panitumumab, erlotinib, gefitinib, lapatinib, and afatinib and the ERBB2 inhibitor can be selected from the group consisting of lapatinib, afatinib, trastuzumab, and pertuzumab. In some aspects, the inhibitor may be a combination of trastuzumab and pertuzumab. Moreover, in some aspects, the analyzing steps may include subjecting the patient sample to at least one of the following: whole genome sequencing, whole exome sequencing, whole transcriptome sequencing, and any other form of sequencing or similar molecular-biology techniques. Further, the method may also comprise assessing effects on the cancer through imaging methods such as tomography following a course of treatment with the therapeutic agent.

Moreover, in some embodiments of the technology, the methodology may also include conducting one or more follow-up examinations of the patient after administration of one or more doses of the target therapeutic. For example, the patient can be tested using tomography techniques, such as CT and/or PET scans, to make determinations about tumor size, tumor growth, tumor shrinkage, disappearance of one or more tumors/lesions, etc. In addition, the method may also include conducting other examinations to assess the patients vital statistics, presence of one or more tumor indicia/markers, affect, etc.

In various embodiments of the present technology, the therapeutic agent may take any physical form necessary depending on a number of factors including the desired method of administration and the physicochemical and stereochemical form taken by the therapeutic agent or pharmaceutically acceptable salts thereof. Such physical forms include a solid, liquid, gas, sol, gel, aerosol, or any other physical form now known or yet to be disclosed. The concept of a therapeutic agent also encompasses the therapeutic agent without any other additive. The physical form of the technology may affect the route of administration and one skilled in the art would know to choose a route of administration that takes into consideration both the physical form of the therapeutic agent and the disorder to be treated. Various pharmaceutical compositions that include the therapeutic agent may be prepared using methodology well known in the pharmaceutical art. A pharmaceutical composition that includes the therapeutic agent may include a second effective compound of a distinct chemical formula from the therapeutic agent. For example, in some embodiments, the pharmaceutical composition can include a combination of any of the aforementioned or later disclosed therapeutic agent described in this instant application. This second effective compound may have the same or a similar molecular target as the target or it may act upstream or downstream of the molecular target of the therapeutic agent with regard to one or more biochemical pathways. In some embodiments, the therapeutic agent may comprise one or more compounds, proteins (e.g., antibodies) or other active ingredients that may provide a therapeutic benefit to an individual with BTC or other diseases.

Pharmaceutical compositions including the therapeutic agent include materials capable of modifying the physical form of a dosage unit. In one nonlimiting example, the composition may include a material that forms a coating that holds in the therapeutic agent. Materials that may be used in such a coating, include for example, sugar, shellac, gelatin, or any other inert coating agent.

Pharmaceutical compositions including the therapeutic agent may be prepared as a gas or aerosol. Aerosols encompass a variety of systems including colloids and pressurized packages. Delivery of a composition in this form may include propulsion of a pharmaceutical composition including the therapeutic agent through use of liquefied gas or other compressed gas or by a suitable pump system. Aerosols may be delivered in single phase, bi-phasic, or tri-phasic systems.

In some aspects of the technology, the pharmaceutical composition including the therapeutic agent may be in the form of a solvate. Such solvates are produced by the dissolution of the therapeutic agent in a pharmaceutically acceptable solvent. Pharmaceutically acceptable solvents include any mixtures of more than one solvent. Such solvents may include pyridine, chloroform, propan-1-ol, ethyl oleate, ethyl lactate, ethylene oxide, water, ethanol, and any other solvent that delivers a sufficient quantity of the disclosed compound to treat the affliction without serious complications arising from the use of the solvent in a majority of patients.

Pharmaceutical compositions that include the therapeutic agent may also include a pharmaceutically acceptable carrier. Carriers include any substance that may be administered with the disclosed compound with the intended purpose of facilitating, assisting, or helping the administration or other delivery of the therapeutic agent. Carriers include any liquid, solid, semisolid, gel, aerosol or anything else that may be combined with the therapeutic agent to aid in its administration. Examples include diluents, adjuvants, excipients, water, oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl cellulose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline, Ringer's solution, isotonic sodium chloride, fixed oils such as synthetic mono or digylcerides, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition including the therapeutic agent may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers are described in "Remington's Pharmaceutical Sciences" by E. W. Martin, hereby incorporated by reference in its entirety.

Methods of administration include, but are not limited to, oral administration and parenteral administration. Parenteral administration includes; but is not limited to intradermal, intramuscular, intraperitoneal, intravenous, subcutaneous, intranasal, epidural, sublingual, intranasal, intracerebral, intraventricular, intrathecal, intravaginal, transdermal, rectal, by inhalation, or topically to the ears, nose, eyes, or skin. Other methods of administration include but are not limited to infusion techniques including infusion or bolus injection; by absorption through epithelial or mucocutaneous linings such as oral mucosa, rectal and intestinal mucosa. Compositions for parenteral administration may be enclosed in ampoule, a disposable syringe or a multiple-dose vial made of glass, plastic or other material.

Administration may be systemic or local. Local administration is administration of the disclosed compound to the area in need of treatment. Examples include local infusion during surgery; topical application, by local injection; by a catheter; by a suppository; or by an implant. Administration may be by direct injection at the site (or former site) of a cancer, tumor, or precancerous tissue or into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include use of an inhaler or nebulizer, formulation with an aerosolizing agent, or via perfusion in a fluorocarbon or synthetic pulmonary surfactant. The disclosed compound may be delivered in the context of a vesicle such as a liposome or any other natural or synthetic vesicle.

A pharmaceutical composition formulae so as to be administered by injection may be prepared by dissolving the therapeutic agent with water so as to form a solution. In addition, a surfactant may be added to facilitate the formation of a homogeneous solution or suspension. Surfactants include any complex capable of non-covalent interaction with the active pharmaceutical agent so as to facilitate dissolution or homogeneous suspension of the therapeutic agent.

Pharmaceutical compositions including the therapeutic agent may be prepared in a form that facilitates topical or transdermal administration. Such preparations may be in the form of a liquid solution, cream, paste, lotion, shake lotion, powder, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Addition of a pharmaceutical composition to cancer cells includes all actions by which an effect of the pharmaceutical composition on the cancer cell is realized. The type of addition chosen will depend upon whether the cancer cells are in vivo, ex vivo, or in vitro, the physical or chemical properties of the pharmaceutical composition, and the effect the composition is to have on the cancer cell. Nonlimiting examples of addition include addition of a solution including the pharmaceutical composition to tissue culture media in which in vitro cancer cells are growing; any method by which a pharmaceutical composition may be administered to an animal including intravenous, per Os, parenteral, or any other of the methods of administration; or the activation or inhibition of cells that in turn have effects on the cancer cells such as immune cells (e.g. macrophages and CD8+ T cells) or endothelial cells that may differentiate into blood vessel structures in the process of angiogenesis or vasculogenesis.

Determination of an effective amount of the therapeutic agent is within the capability of those skilled in the art, especially, in light of the detailed disclosure provided herein. The effective amount of a therapeutic agent used to affect a particular purpose as well as a pharmacologically acceptable dose determined by toxicity, excretion, and overall tolerance may be determined in cell cultures or experimental animals by pharmaceutical and toxicological procedures either known now by those skilled in the art or by any similar method yet to be disclosed. One example is the determination of the $IC_{50}$ (half maximal inhibitory concentration) of the pharmaceutical composition in vitro in cell lines or target molecules. Another example is the determination of the $LD_{50}$ (lethal dose causing death in 50% of the tested animals) of the therapeutic agent in experimental animals. The exact techniques used in determining an effective amount will depend on factors such as the type and physical/chemical properties of the therapeutic agent, the property being tested, and whether the test is to be performed in vitro or in vivo. The determination of an effective amount of a therapeutic agent will be well known to one of skill in the art who will use data obtained from any tests in making that determination. Determination of an effective amount of disclosed compound for addition to a cancer cell also includes the determination of an effective therapeutic amount, including the formulation of an effective dose range for use in vivo, including in humans.

Treatment is contemplated in living entities including but not limited to mammals (particularly humans) as well as other mammals of economic or social importance, including those of an endangered status. Further examples include livestock or other animals generally bred for human consumption and domesticated companion animals.

The toxicity and therapeutic efficacy of a therapeutic agent may be determined by standard pharmaceutical procedures in cell cultures or animals. Examples include the determination of the IC.sub.50 and the LD.sub.50 for a subject compound. The data obtained from these cell culture assays and animal studies can be used in formulating a range of dosage for use in human. The dosage may vary depending upon the dosage form employed and the route of administration utilized.

The effective amount of the therapeutic agent to result in the slowing of expansion of the cancer cells would preferably result in a concentration at or near the target tissue that is effective in slowing cellular expansion in cancer cells, but have minimal effects on non-cancer cells, including non-cancer cells exposed to radiation or recognized chemotherapeutic chemical agents. Concentrations that produce these effects can be determined using, for example, apoptosis markers such as the apoptotic index and/or caspase activities either in vitro or in vivo.

Treatment of a condition is the practice of any method, process, or procedure with the intent of halting, inhibiting, slowing or reversing the progression of a disease, disorder or condition, substantially ameliorating clinical symptoms of a disease disorder or condition, or substantially, preventing the appearance of clinical symptoms of a disease, disorder or condition, up to and including returning the diseased entity to its condition prior to the development of the disease.

The addition of a therapeutically effective amount of the therapeutic agent encompasses any method of dosing of a composition. Dosing of the disclosed compound may include single or multiple administrations of any of a number of pharmaceutical compositions that include the disclosed therapeutic agent as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A final dosing regimen including the regularity of and mode of administration will be dependent on any of a number of factors including but not limited to the subject being treated; the severity of the affliction; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

Pharmaceutical compositions that include the therapeutic agent may be administered prior to, concurrently with, or after administration of a second pharmaceutical composition that may or may not include the therapeutic agent. If the compositions are administered concurrently, they may be administered within one minute of each other. If not administered concurrently, the second pharmaceutical composition may be administered a period of one or more minutes, hours, days, weeks, or months before or after the pharmaceutical composition that includes the compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration, in order to reduce the development of resistance to one or more of the compositions, to avoid or reduce the side effects of one or more of the compositions, and/or to improve the efficacy of the treatment.

The technology further encompasses kits that facilitate the administration of the pharmaceutical composition to a diseased entity. An example of such a kit includes one or more unit dosages of the therapeutic agent. The unit dosage would be enclosed in a preferably sterile container and would be comprised of the disclosed compound and a pharmaceutically acceptable carrier. In another aspect, the unit dosage would comprise one or more lyophilates of the compound. In this aspect of the technology, the kit may include another preferably sterile container enclosing a solution capable of dissolving the lyophilate. However, such a solution need not be included in the kit and may be obtained separately from the lyophilate. In another aspect, the kit may include one or more devices used in administrating the unit dosages or a pharmaceutical composition to be used in combination with the compound. Examples of such devices include, but are not limited to, a syringe, a drip bag, a patch or an enema. In some aspects of the technology, the device comprises the container that encloses the unit dosage.

Pharmaceutical compositions including the therapeutic agent may be used in methods of treating cancer. Such methods involve the administration of a therapeutic amount of a pharmaceutical composition that includes the therapeutic agent and/or a pharmaceutically acceptable salt thereof to a mammal, preferably a mammal in which a cancer has been diagnosed.

A therapeutic amount further includes the prevention of progression of the cancer to a neoplastic, malignant or metastatic state. Such preventative use is indicated in conditions known or suspected of preceding progression to cancer, in particular, where non- or precancerous cell growth consisting of hyperplasia, metaplasia, or most particularly, dysplasia has occurred (for review of such abnormal growth conditions, see Robbins and Angell, 1976, Basic Pathology, 2d Ed., W. B. Saunders Co., Philadelphia, pp. 68-90, incorporated by reference). Hyperplasia is a form of controlled cell proliferation involving an increase in cell number in a tissue or organ, without significant alteration in structure or activity. For example, endometrial hyperplasia often precedes endometrial cancer and precancerous colon polyps often transform into cancerous lesions. Metaplasia is a form of controlled cell growth in which one type of adult or fully differentiated cell substitutes for another type of adult cell. Metaplasia can occur in epithelial or connective tissue cells. A typical metaplasia involves a somewhat disorderly metaplastic epithelium. Dysplasia is frequently a forerunner of cancer, and is found mainly in the epithelia; it is the most disorderly form of non-neoplastic cell growth, involving a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively or in addition to the presence of abnormal cell growth characterized as hyperplasia, metaplasia, or dysplasia, the presence of one or more characteristics of a transformed phenotype or of a malignant phenotype, displayed in vivo or displayed in vitro by a cell sample derived from a patient can indicate the desirability of prophylactic/therapeutic administration of the pharmaceutical composition that includes the compound. Such characteristics of a transformed phenotype include morphology changes, looser substratum attachment, loss of contact inhibition, loss of anchorage dependence, protease release, increased sugar transport, decreased serum requirement, expression of fetal antigens, disappearance of cell surface proteins, etc. Further examples include leukoplakia, featuring a benign-appearing hyperplastic or dysplastic lesion of the epithelium, or Bowen's disease, a carcinoma in situ. Both of these are pre-cancerous lesions indicative of the desirability of prophylactic intervention. In another example, fibrocystic disease including cystic hyperplasia, mammary dysplasia, adenosis, or benign epithelial hyperplasia is indicates desirability of prophylactic intervention.

EXAMPLES

Examples that represent different aspects of the technology follow. Such examples should not be construed as limiting the scope of the disclosure. Alternative mechanistic pathways and analogous structures within the scope of the technology would be apparent to those skilled in the art.

To comprehensively explore the genetic basis of cholangiocarcinoma, with emphasis on elucidation of therapeutically relevant targets, integrated whole genome, whole exome, and whole transcriptome analyses were performed on tumors from patients with cholangiocarcinoma. In the instant matter, samples from a patient's tumor and a normal sample, generally in accord with the methodologies contained herein. Tables 1-3 provides sequencing metrics from a 50-year old patient with advanced, treated refractory cholangiocarcinoma.

Exome sequencing: Genomic DNA for each sample was fragmented to a target size of 150-200 bp on the Covaris E210. 100 ng of fragmented product was run on TAE gel to verify fragmentation. The remaining 1 µg of fragmented DNA was prepared using Agilent's SureSelect$^{XT}$ and SureSelect$^{XT}$ Human All Exon 50 Mb kit (catalog # G7544C). Alternatively, one of the following protocols may have also been used: (i) Genomic tumor and normal DNA was used to create exome libraries using Illumina's Nextera Exome Enrichment kit (catalog # FC-121-1204) following the manufacturer's protocol; (ii) Tumor and germline DNA sample was used to generate separate exome libraries such that libraries were prepared using Illumina's TruSeq DNA Sample Prep Kit and Exome Enrichment Kit (catalog # FC-121-1008) following the manufacturer's protocols; and (iii) Genomic tumor and normal DNA was fragmented on the Covaris E210 to a target size of 150-200 bp. Exome libraries were prepared with Agilent's (Santa Clara, Calif.) SureSelectXT Human All Exon V4 library preparation kit (catalog #5190-4632) and SureSelectXT Human All Exon V4+UTRs (catalog #5190-4637) following the manufacturer's protocols.

Whole Genome sequencing: Genomic DNA was used to generate separate long insert whole genome libraries for each sample using Illumina's (San Diego, Calif.) TruSeq DNA Sample Prep Kit (catalog # FC-121-2001). In summary, genomic DNAs are fragmented to a target size of 900-1000 by on the Covaris E210. 100 ng of the sample was run on a 1% TAE gel to verify, fragmentation. Samples were end repaired and purified with Ampure XP beads using a 1:1 bead volume to sample volume ratio, and ligated with indexed adapters. Samples are size selected at approximately 1000 bp by running samples on a 1.5% TAE gel and purified using Bio-Rad Freeze 'n Squeeze columns and Ampure XP beads. Size selected products are then amplified using PCR and products were cleaned using Ampure XP beads.

Paired end sequencing: Libraries with a 1% phiX spike-in were used to generate clusters on HiSeq Paired End v3 flowcells on the Illumina cBot using Illumina's TruSeq PE Cluster Kit v3 (catalog # PE-401-3001). Clustered flowcells were sequenced by synthesis on the Illumina HiSeq 2000 using paired-end technology and Illumina's TruSeq SBS Kit.

Somatic mutation validation: Mutations of potential clinical relevance were confirmed in a Clinical Laboratory Improvement Amendments (CLIA) laboratory with Sanger sequencing or quantitative PCR.

TABLE 1

| Exome | |
|---|---:|
| Tumor | |
| Aligned Reads | 287,076,216 |
| Average Target Coverage | 759 |
| % Target Base at 10× | 99% |
| % Target Base at 20× | 99% |
| % Target Base at 30× | 98% |
| % Target Base at 40× | 97% |
| % Target Base at 50× | 96% |
| % Target Base at 100× | 85% |
| Normal | |
| Aligned Reads | 255,319,730 |
| Average Target Coverage | 234 |
| Target Base at 10× | 99% |
| % Target Base at 20× | 98% |
| % Target Base at 30× | 97% |
| % Target Base at 40× | 96% |
| % Target Base at 50× | 95% |
| % Target Base at 100× | 81% |

TABLE 2

| Whole Genome | |
|---|---:|
| Tumor | |
| Clonal Coverage | 37 |
| Aligned Reads | 290,151,871 |
| Aligned Bases | 31,407,755,16 |
| Genome Size | 3,095,693,981 |
| Base Coverage | 10 |
| Normal | |
| Colonal Coverage | 32 |
| Aligned Reads | 245,024,831 |
| Aligned Bases | 26,528,925,092 |
| Genome Size | 3,095,693,981 |
| Base Coverage | 9 |

For whole genome and exome sequencing, fastq files were aligned with BWA 0.6.2 to GRCh37.62 and the SAM output were converted to a sorted BAM file using SAMtools 0.1.18. BAM files were then processed through indel realignment, mark duplicates, and recalibration steps in this order with GATK 1.5 where dpsnp135 was used for known SNPs and 1000 Genomes' ALL.wgs.low_coverage_vqsr.20101.123 was used for known indels.

Lane level sample BAMs were then merged with Picard 1.65 if they were sequenced across multiple lanes. Comparative variant calling for exome data was conducted with Seurat (See Reference 22). Previously described copy number and translocation detection were applied to the whole genome long insert sequencing data and these are made available through the Internet site github.com/davcraig75/tgen_somaticsSV.

Copy number detection was based on a log 2 comparison of normalized physical coverage (or clonal coverage) across tumor and normal whole genome long-insert sequencing data, where physical coverage was calculated by considering the entire region a paired-end fragment spans on the genome, then the coverage at 100 bp intervals was kept. Normal and tumor physical coverage was then normalized, smoothed and filtered for highly repetitive regions prior to calculating the log 2 comparison. Translocation detection was based on discordant read evidence in the tumor whole genome sequencing data compared to its corresponding normal data. In order for the structural variant to be called there needs to be greater than 7 read pairs mapping to both sides of the breakpoint. The unique feature of the long-insert whole-genome sequencing was the long overall fragment size (~1 kb), where by two 100 bp reads flank a region of ~800 bp. The separation of forward and reverse reads increases the overall probability that the read pairs do not cross the breakpoint and confound mapping.

Total RNA was used to generate whole transcriptome libraries for RNA sequencing. Using the Nugen Ovation RNA-Sect System v2 (catalog #7102), total RNA was used to generate double stranded cDNA, which was subsequently amplified using Nugen's SPIA linear amplification process. Amplified products were cleaned using Qiagen's QIAquick PCR Purification Kit and quantitated using Invitrogen's Quant-iT Picogreen. 1 µg of amplified cDNA was fragmented on the Covaris E210 to a target size of 300 bp. TruSeq DNA Sample Preparation Kit was used to prepare libraries from 1 µg amplified cDNA. Alternatively, total RNA for each sample was used to generate RNA sequencing libraries using Illumina's TruSeq RNA Sample Prep Kit V2 (catalog # RS-122-2001) following the manufacturer's protocol.

TABLE 3

| RNA | |
|---|---|
| Tumor | |
| Aligned Reads | 287,076,216 |
| Aligned Bases | 22,626,251,500 |
| % Ribosomal Bases | 0% |
| % Coding Bases | 61% |
| % UTR Bases | 28% |
| % Intronic Bases | 4% |
| % Intergenic Bases | 6% |
| % MRNA Bases | 90% |

For RNA sequencing, lane level fastq files were appended together if they were across multiple lanes. These fastq files were then aligned with TopHat 2.0.6 to GRCh37.62 using ensembl.63.genes.gtf as GU file. Changes in transcript expression were calculated with Cuffdiff 2.0.2. For novel fusion discovery reads were aligned with TopHat-Fusion 2.0.6 (See reference 23) (patients 2, 3, 4 and 6). In addition, Chimerascan 0.4.5 (See reference 24) was used to detect fusions in patient 1, deFuse 5.0 (See reference 25) used in patients 2, 3 and 5 and SnowShoes (See reference 25) for patients 2 and 5.

As illustrated in FIGS. 1A-X and 2, the presence of an RBPMS-NRG1 fusion was identified using long insert whole genome sequencing, whole transcriptome sequencing (RNA sequencing), and array comparative genomic hybridization. After identification of this NRG1 fusion event/genomic aberration, the patient was treated with a combination of trastuzumab and pertuzumab, which are both antibody-based therapeutic agents that target ERBB2. In particular, pertuzumab disrupts the ability of ERBB2 to dimerize. As demonstrated in the front view of the patient in FIG. 3 and cross-sectional view of the same patient in FIG. 4, at approximately eight weeks after initiation of the combination therapy, imaging with PET scan indicated the disappearance of multiple tumor lesions, as well as a reduction in size of other lesions that persisted. The patient reported an increase in performance status, appetite, and a reduction in pain. In addition, at this same time point, tumor markers CA19-9, carcinoembryonic antigen, and alpha-fetoprotein were reduced by about 97%, 59.4%, and 70.5%, respectively, from baseline. At baseline, both the tumor markers carcinoembryonic antigen and alpha-fetoprotein were above normal limits and, after 8 weeks of treatment, the levels of both tumor markers were reduced into normal range. To the investigators' knowledge, the successful intervention using trastuzumab and pertuzumab in a patient with an NRG1 fusion delineates the first instance of this successful combination.

Furthermore, mate-pair sequencing and flow sorting-enabled array comparative genomic hybridization (aCGH) uncovered the presence of other NRG1 genomic aberrations (e.g., fusions, rearrangements, etc.) in hepatocellular cancer, colon cancer, breast cancer, pancreatic cancer, lung cancer, and ovarian cancer.

In the foregoing description, the technology has been described with reference to specific exemplary embodiments. Various modifications and changes may be made, however, without departing from the scope of the present technology as set forth. The description and figures are to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present technology and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises", "comprising", or any variation thereof, are intended to reference a non-exclusive inclusion, such that a process, method, article, composition, system, or apparatus that comprises a list of elements does not include only those elements recited, but may also include other elements not expressly listed or inherent to such process, method, article, composition, system, or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to an exemplary embodiment. However, changes and modifications may be made to the exemplary embodiment without departing from the scope of the present technology. These and other changes or modifications are intended to be included within the scope of the present technology.

REFERENCES

So as to reduce the complexity and length of the Detailed Description, the following references are expressly incorporated by reference to the extent they do not conflict with the present disclosure:

1. Shin H R, Lee C U, Park H Seol S Y, Chung J M, et al. (1996) Hepatitis B and C virus, Clonorchis sinensis for the risk of liver cancer: a case-control study in Pusan, Korea. International journal of epidemiology 25: 933-940.
2. Watanapa P (1996) Cholangiocarcinoma in patients with opisthorchiasis. The British journal of surgery 83: 1062-1064.
3. Watanapa P, Watanapa. W B (2002) Liver fluke-associated cholangiocarcinoma. The British journal of surgery 89: 962-970.
4. Bergquist A, Ekbom A, Olsson R, Kornfeldt D, Loof L, et al. (2002) Hepatic and extrahepatic malignancies in primary sclerosing cholangitis. Journal of hepatology 36: 321-327.
5. Bergquist A, Glaumann H, Persson B, Broome U (1998) Risk factors and clinical presentation of hepatobiliary carcinoma in patients with primary sclerosing cholangitis: a case-control study. Hepatology 27: 311-316.
6. Burak K, Angulo P, Pasha T M, Egan K, Petz J, et al. (2004) incidence and risk factors for cholangiocarcinoma in primary sclerosing cholangitis. The American journal of gastroenterology 99: 523-526.
7. Claessen M M, Vleggaar F P, Tytgat K M, Siersema P D, van Buuren H R (2009) High lifetime risk of cancer in primary sclerosing cholangitis. Journal of hepatology 50: 158-164.
8. Visser B C, Suh I, Way L W, Kang S M (2004) Congenital choledochal cysts ifs adults. Archives of surgery 139: 855-860 discussion 860-852.
9. Hsing A W, Zhang M, Rashid A, McGlynn K A, Wang B S. et al. (2008) Hepatitis B and C virus infection and the risk of biliary tract cancer: a population-based study in China. International journal of cancer Journal international du cancer 122: 1849-1853.
10. Kobayashi M, Ikeda K, Saitoh S, Suzuki F, Tsubota A, et al. (2000) Incidence of primary cholangiocellular carcinoma of the liver in japanese patients with hepatitis C virus-related cirrhosis. Cancer 88: 2471-2477.
11. Liu X F, Zou S Q, Qiu F Z (2003) Pathogenesis of cholangiocarcinoma in the porta hepatis and infection of hepatitis virus. Hepatobiliary & pancreatic diseases international: HBPD INT 2: 285-289.
12. Shaib Y H, El-Serag B. Davila J A, Morgan R, McGlynn K. A (2005) Risk factors of intrahepatic cholangiocarcinoma in the United States: a case-control study. Gastroenterology 128: 620-626.
13. Wetzel T M, Graubard B I, El-Serag H B, Shaib Y H, Hsing, A W, et al. (2007) Risk factors for intrahepatic and extrahepatic cholangiocarcinoma in the United States: a population-based case-control study. Clinical gastroenterology and hepatology: the official clinical practice journal of the American Gastroenterological Association 5: 1221-1228.
14. Yamamoto S, Kubo S, Hai S, Uenishi T, Yamamoto T, et al. (2004) Hepatitis C virus infection as a likely etiology of intrahepatic cholangiocarcinoma. Cancer science 95: 592-595,
15. Donato F, Gelatti U, Tagger A, Favret M, Ribero M L, et al. (2001) Intrahepatic cholangiocarcinoma and hepatitis C and B virus infection, alcohol intake, and hepatolithiasis: a case-control study in Italy. Cancer causes & control: CCC 12: 959-964.
16. Lee C C, Wu C Y, Chen G H (2002) What is the impact of coexistence of hepatolithiasis on cholangiocarcinoma? Journal of gastroenterology and hepatology 17: 1015-1020.
17. Becker N, Liebermann D, Wesch K, Van Kaick G (2008) Mortality among Thorotrast-exposed patients and an unexposed comparison group in the German Thorotrast study. European journal of cancer 44: 1259-1268.
18. Travis L B, Hauptmann M, Gaul L K, Storm H Goldman M B, et al. (2003) Site-specific cancer incidence and mortality after cerebral angiography with radioactive thorotrast. Radiation research 160: 691-706.
19. Khan S Thomas H C, Davidson B R, Taylor-Robinson S D (2005) Cholangiocarcinoma. Lancet 366: 1303-1314.
20. Valle J Wasan H. Palmer D H, Cunningham D, Anthoney A, et al, (2010) Cisplatin plus gemcitabine versus gemcitabine for biliary tract cancer. The New England journal of medicine 362: 1273-1281.
21. Craig D W, O'Shaughnessy J A, Kiefer J A, Aldrich J, Sinari S, et al. (2013) Genome and transcriptome sequencing in prospective metastatic triple-negative breast cancer uncovers therapeutic vulnerabilities. Mol Cancer Ther 12: 104-116.
22. Christoforides A, Carpten J D, Weiss G J, Demeure M J, Von Hoff D D, et al. (2013) Identification of somatic mutations in cancer through Bayesian-based analysis of sequenced genome pairs. BMC Genomics 14: 302.
23. Kim D, Salzberg S L (2011) TopHat-Fusion: an algorithm for discovery of novel fusion transcripts. Genome Biol 12: R72.
24. Iyer M K. Chinnaiyan A M, Maher C A (2011) ChimeraScan: a tool for identifying chimeric transcription in sequencing data. Bioinformatics 27: 2903-2904.
25. McPherson A, Hormozdiari F, Zayed A, Giuliany R, Ha G, et al. (2011) deFuse: an algorithm for gene fusion discovery in tumor RNA-Seq data. PLoS Comput Biol 7: e1001138.
26. Asmann Y W, Hossain A, Necela B M, Middha S, Kalari K R, et al. (2011) A novel bioinformatics pipeline for identification and characterization of fusion transcripts in breast cancer and normal cell lines. Nucleic Acids Res 39: e100.
27. Diep C H, Zucker K M, Hostetter G, Watanabe A, Hu C, et al. (2012) Down-regulation of Yes Associated Protein 1

28. L. Fernandez Cuesta et (2014) CD74-NRG1 Fusions in Lung Adenocarcinoma. Cancer Discovery 4(4): 415-422.
29. T. Nakaoku of al. (2014) Druggable Oncogene Fusions In Invasive Mucinous Lung Adenocarcinoma. Clin. Cancer Research 12: 3087-93.
30. S. Dhanasekaran et al. (2014) Transcriptome meta-analysis of lung cancer reveals recurrent aberrations in NRG1 and Hippo pathway genes. Nature Communications 5: 5893.
31. L. Fernandez-Cuesta and R. K. Thomas (2015) Molecular Pathways: Targeting NRG1 Fusions in Lung Cancer. Clin. Cancer Research 21(9): 1989-94.

The invention claimed is:

1. A method of treating a patient with cholangiocarcinoma cancer, the method comprising the steps of:
    analyzing a sample from a patient with cholangiocarcinoma cancer for a DNA translocation in chromosome 8 band 12 p;
    identifying a RBPMS-NRG1 fusion event transcribed by the DNA translocation in chromosome 8 band 12 p having a breakpoint between the 5' end of exon 5 of the RBPMS portion and the 3' end of exon 2 of the NRG1 portion, wherein the NRG1 portion of the RBPMS-NRG1 fusion event retains a EGF-like domain on the NRG1 portion; and
    administering to the patient, having the RBPMS-NRG1 fusion event, a treatment of a therapeutic agent comprising at least one EGFR inhibitor that is targeted for the EGF-like domain of the NRG1 portion of the RBPMS-NRG1 fusion event.

2. The method of claim 1, wherein the at least one EGFR inhibitor is at least one of cetuximab, panitumumab, Sym004, MM-151, mAb 806, mAb 528, MEHD794A, gefitinib, erlotinib, lapatinib, afatinib, PD153035, and AG1478.

3. The method of claim 1 further comprising administering to the patient, having the RBPMS-NRG1 fusion event, a treatment of a second therapeutic agent comprising at least one ERBB2 inhibitor that is targeted for the EGF-like domain of the NRG1 portion of the RBPMS-NRG1 fusion event.

4. The method of claim 3, wherein the at least one ERBB2 inhibitor is at least one of lapatinib, afatinib, trastuzumab and pertuzumab.

5. The method of claim 1, wherein the therapeutic agent further comprises at least one ERBB2 inhibitor that is targeted for the EGF-like domain of the NRG1 portion of the RBPMS-NRG1 fusion event.

6. The method of claim 5, wherein the at least ERBB2 inhibitor is at least one of lapatinib, afatinib, trastuzumab, and pertuzumab.

7. The method of claim 1, wherein the analyzing step comprises subjecting the sample to at least one of the following: whole genome sequencing, whole exome sequencing, and whole transcriptome sequencing.

8. The method of claim 1 further comprising assessing growth inhibition of the cholangiocarcinoma cancer in the patient through tomography following a course of treatment of the therapeutic agent.

9. A method of inhibiting cancer cell growth, comprising:
    identifying a cholangiocarcinoma cancer cell containing a RBPMS-NRG1 fusion protein transcribed from an inter-chromosomal DNA translocation in chromosome 8 band p12 of the cell, and having a EGF-like domain on the NRG1 portion of the fusion protein, wherein the RBPMS-NRG1 fusion includes exons 1-5 of RBPMS and exons 1 and 2 of NRG1;
    contacting the cholangiocarcinoma cancer cell containing the RBPMS-NRG1 fusion protein with a therapeutic agent comprising at least one EGFR inhibitor that is targeted for the EGF-like domain of the NRG1 portion of the RBPMS-NRG1 fusion event.

10. The method of claim 9, wherein the at least one EGFR inhibitor is at least one of cetuximab, panitumumab, Sym004, MM-151, mAb 806, mAb 528, MEHD794A, gefitinib, erlotinib, lapatinib, afatinib, PD153035, and AG1478.

11. The method of claim 9 further comprising contacting the cholangiocarcinoma cancer cell containing the RBPMS-NRG1 fusion protein with a second therapeutic agent comprising at least ERBB2 inhibitor that is targeted for the EGF-like domain of the NRG1 portion of the RBPMS-NRG1 fusion protein.

12. The method of claim 11, wherein the at least one ERBB2 inhibitor is at least one of lapatinib, afatinib, trastuzumab and pertuzumab.

13. The method of claim 9, wherein the therapeutic agent further comprises at least one ERBB2 inhibitor that is targeted for the EGF-like domain of the NRG1 portion of the RBPMS-NRG1 fusion protein.

14. The method of claim 13, wherein the at least one ERBB2 inhibitor is at least one of lapatinib, afatinib, trastuzumab, and pertuzumab.

15. The method of claim 9, wherein the identifying step comprises subjecting the cholangiocarcinoma cancer cell to at least one of the following: whole genome sequencing, whole exome sequencing, and whole transcriptome sequencing.

16. The method of claim 9 further comprising assessing growth inhibition of the cholangiocarcinoma cancer cell containing the RBPMS-NRG1 fusion protein through tomography following a course of treatment of the therapeutic agent.

17. A method for selecting a chemotherapy regimen for a patient to treat cholangiocarcinoma, the method comprising the steps of:
    collecting a genetic sample from a patient's cholangiocarcinoma tumor;
    analyzing the genetic sample for a RBPMS-NRG1 fusion transcribed from an interchromosomal DNA translocation in chromosome 8 band p12;
    identifying a RBPMS-NRG1 fusion in the genetic sample, wherein the NRG1 portion of the fusion comprises a EGF-like domain on the NRG1 portion receptor of the fusion, wherein the RBPMS-NRG1 fusion includes exons 1-5 of RBPMS and exons 1 and 2 of NRG1;
    selecting a chemotherapy regimen for the patient, having the RBPMS-NRG1 fusion, comprising at least one treatment with an EGFR inhibitor that is targeted for the EGF-like domain of the NRG1 portion of the RBPMS-NRG1 fusion event; and
    treating the patient with a therapeutic agent comprising the EGFR inhibitor that is targeted for the EGF-like domain of the NRG1 portion of the RBPMS-NRG1 fusion event.

18. The method according to claim 17 further comprising treating the patient with a therapeutic agent comprising the EGFR inhibitor.

19. The method of claim 18, wherein the EGFR inhibitor at least one of cetuximab, panitumumab, Sym004, MM-151, mAb 806, mAb 528, MEHD794A, gefitinib, erlotinib, lapatinib, afatinib, PD153035, and AG1478.

20. The method of claim 18, wherein the therapeutic agent further comprises at least one ERBB2 inhibitor that is targeted for the EGF-like domain of the NRG1 portion of the RBPMS-NRG1 fusion.

21. The method of claim 20, wherein the at least one ERBB2 inhibitor is at least one of lapatinib, afatinib, trastuzumab, and pertuzumab.

22. The method of claim 18 further comprising assessing growth inhibition of the patient's cholangiocarcinoma tumor through tomography following a course of treatment with the therapeutic agent.

23. The method of claim 17, wherein the chemotherapy regimen for the patient, having the RBPMS-NRG1 fusion, further comprises at least one treatment with an ERBB2 inhibitor that is targeted for the EGF-like domain of the of the NRG1 portion of the RBPMS-NRG1 fusion.

24. The method according to claim 23, further comprising treating the patient with a therapeutic agent comprising the ERBB2 inhibitor that is targeted for the EGF-like domain of the NRG1 portion of the RBPMS-NRG1 fusion.

25. The method of claim 24, wherein the ERBB2 inhibitor is at least one of lapatinib, afatinib, trastuzumab, and pertuzumab.

26. The method of claim 24 further comprising assessing growth inhibition of the patient's cholangiocarcinoma tumor through tomography following a course of treatment with the therapeutic agent.

* * * * *

UNITED STATES PATENT AND TRADEMARK OFFICE
CERTIFICATE OF CORRECTION

| | |
|---|---|
| PATENT NO. | : 11,866,789 B2 |
| APPLICATION NO. | : 17/411447 |
| DATED | : January 9, 2024 |
| INVENTOR(S) | : Sara Byron et al. |

It is certified that error appears in the above-identified patent and that said Letters Patent is hereby corrected as shown below:

On the Title Page

Item (73), please add the following entity to the Assignee section:
Mayo Foundation for Medical Education and Research, Rochester, MN (US)

Signed and Sealed this
Nineteenth Day of March, 2024

Katherine Kelly Vidal
*Director of the United States Patent and Trademark Office*